United States Patent [19]

Myers

[11] Patent Number: 5,408,008

[45] Date of Patent: Apr. 18, 1995

[54] PIPERIDINYL PHTHALIMIDE HINDERED AMINE LIGHT STABILIZERS

[75] Inventor: Terry N. Myers, Williamsville, N.Y.

[73] Assignee: Elf Atochem North America, Inc., Philadelphia, Pa.

[21] Appl. No.: 112,749

[22] Filed: Aug. 26, 1993

Related U.S. Application Data

[60] Division of Ser. No. 317,372, Mar. 1, 1989, Pat. No. 5,241,067, which is a continuation-in-part of Ser. No. 60,878, Jun. 12, 1987, abandoned.

[51] Int. Cl.$^6$ .................................................. C08F 8/30
[52] U.S. Cl. ............................. 525/328.2; 525/328.3; 525/328.5; 525/329.1; 525/329.3; 525/375; 525/408; 525/437; 525/447; 525/474
[58] Field of Search ............... 525/328.2, 328.3, 328.5, 525/329.1, 329.3, 408, 437, 447, 474

[56] References Cited

U.S. PATENT DOCUMENTS

| | | |
|---|---|---|
| 3,483,276 | 12/1969 | Mahlman . |
| 3,904,581 | 9/1975 | Murayama et al. . |
| 4,097,551 | 6/1978 | DiGiulio et al. . |
| 4,309,546 | 1/1982 | Karrer . |
| 4,336,183 | 6/1982 | Nakahara et al. . |
| 4,356,307 | 10/1982 | Kelkenberg et al. . |
| 4,486,570 | 12/1984 | Lordi et al. . |
| 4,506,056 | 3/1985 | Gaylord . |
| 4,569,997 | 2/1986 | Karrer . |

FOREIGN PATENT DOCUMENTS

| | | |
|---|---|---|
| 1190038 | 7/1985 | Canada . |
| 2145100 | 3/1985 | United Kingdom . |

OTHER PUBLICATIONS

*Kirk–Othmer Encyclopedia of Chemical Technology*, vol. 23, pp. 615–627.
*Polymerization Mechanisms and Processes*, vol. 18, pp. 720–744.

Primary Examiner—Bernard Lipman
Attorney, Agent, or Firm—Panitch Schwarze Jacobs & Nadel

[57] ABSTRACT

Hindered amine light stabilizers are provided in which the hindered amine is contained in a unit of formula

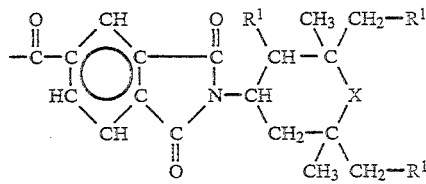

where X is

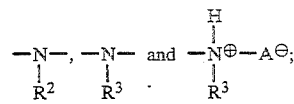

and $R^1$, $R^2$, $R^3$, and A are as defined as in the Summary of the Invention. Unique polymeric and non-polymeric compounds containing this unit are useful as additives for the stabilization of polymeric compositions which are normally subject to thermal, oxidative or actinic light degradation.

15 Claims, No Drawings

PIPERIDINYL PHTHALIMIDE HINDERED AMINE LIGHT STABILIZERS

CROSS-REFERENCE TO RELATED APPLICATIONS

This is a division of U.S. patent application Ser. No. 317,372, filed Mar. 1, 1989, now U.S. Pat. No. 5,241,067, which was a continuation-in-part of U.S. patent application Ser. No. 60,878, filed Jun. 12, 1987, now abandoned.

Background of the Invention

This invention relates to hindered amine light stabilizers in which the hindered amine is attached to the nitrogen of an imide which is attached to an aromatic group containing a carboxylic acid or derivative thereof.

Hindered amine light stabilizers (hereinafter referred to as "HALS") are a well-known class of compounds known to prevent and retard the degradation of polymers in which they are incorporated (*Kirk-Othmer Encyclopedia of Chemical Technology*, 3rd Ed., Vol. 23, "UV Stabilizers", pp. 615–627). Many patents on HALS additives and monomers have been issued, e.g., U.S. Pat. No. 4,336,183. The fundamental HALS functionality is a rather small molecular ensemble, generally water soluble; this prohibits use of simple, low molecular weight HALS because they are readily leached from the polymer substrate upon exposure to moisture.

HALS imides such as N-(2,2,6,6-tetramethyl-4-piperidinyl)maleimide are known and have been used to prepare HALS-containing copolymers (as in U.S. Pat. No. 4,569,997 and British Patent Application Publication No. 2,145,100 A). Other N-(2,2,6,6-tetramethyl-4-piperidinyl)imides are disclosed in U.S. Pat. No. 4,356,307, but the disclosed compounds are nonaromatic imides. N-(2,2,6,6-tetramethyl-4-piperidinyl)phthalimide and N,N'-bis-(2,2,6,6-tetramethyl-4-piperidinyl)pyromellitic diimide have been disclosed as polymer stabilizers in U.S. Pat. No. 3,904,581, although neither compound was prepared nor tested.

No reference to the instant invention could be found in the literature.

Definitions

As used herein, the term "acyl" refers to a substituent derived from a carboxylic acid group by removing the OH of the carboxyl group thereby providing a free valence, i.e. the acyl group derived from a generalized carboxylic acid Q—C(=O)—OH would have the formula Q—C(=O)— and would be referred to herein as a "Q acyl" group.

As used herein, the term "aliphatic," whether used alone or when incorporated as part of another term in naming a radical, such as "aliphatic acyl" or "araliphatic," for example, denotes an organic chemical radical characterized by straight-chain or branched-chain arrangement of the constituent carbon atoms, wherein the radical has the indicated number of carbon atoms. As used herein, the term "aryl," whether used alone or when incorporated as part of another term in naming a radical, such as "aryl acy" or "araliphatic," for example, denotes a carbocyclic aromatic ring structure, wherein the radical has the indicated number of carbon atoms.

As used herein, the terms "polymer" and "polymeric composition(s)" include homopolymers or any type of copolymers.

When any generalized functional group or index, such as $R^1$, $R^2$, d, q, etc., appears more than once in a general formula, the meaning of each is independent of one another.

SUMMARY OF THE INVENTION

This invention is directed to compounds of general formula

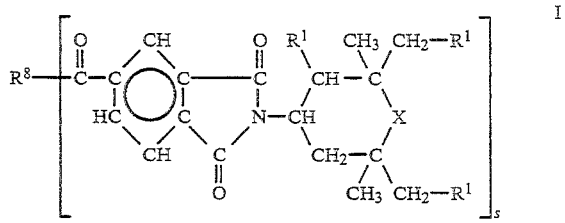

and derivatives thereof, where $R^1$ is hydrogen or substituted or unsubstituted alkyl of 1–4 carbons. Preferably, $R^1$ is hydrogen or methyl. Most preferably, $R^1$ is hydrogen.

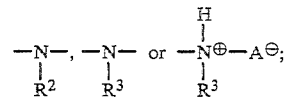

$R^2$ is oxyl, hydroxy, substituted or unsubstituted aliphatic acyl of 1–20 carbons, substituted or unsubstituted alicyclic acyl of 6–14 carbons, substituted or unsubstituted aryl acyl of 7–11 carbons, substituted or unsubstituted araliphatic acyl of 7–22 carbons, —C(=O)—N($R^4$)($R^5$) or —C(=O)—O—$R^6$. Preferably, $R^2$ is substituted or unsubstituted alkanoyl of 2–5 carbons, aliphatic acyl of 2–5 carbons, substituted or unsubstituted aryl acyl of 7–11 carbons or substituted or unsubstituted araliphatic acyl of 7–22 carbons. Most preferably, $R^2$ is acetyl, substituted or unsubstituted benzoyl or —C(=O)—O—$R^6$.

$R^3$ is hydrogen, substituted or unsubstituted aliphatic of 1–20 carbons, substituted or unsubstituted araliphatic of 7–22 carbons, alkoxyalkyl of 2–21 carbons or —CH$_2$—C(=O)—O—$R^7$. Preferably, $R^3$ is hydrogen, substituted or unsubstituted alkyl of 1–4 carbons, substituted or unsubstituted alkoxyalkyl of 2–6 carbons, substituted or unsubstituted araliphatic of 7–10 carbons, allyl or —CH$_2$—C(=O)—O—$R^7$. Most preferably, $R^3$ is hydrogen, substituted or unsubstituted alkyl of 1–4 carbons, allyl, benzyl or —CH$_2$—C(=O)—O—$R^7$.

$R^4$, $R^5$ and $R^7$ are independently hydrogen, substituted or unsubstituted aliphatic of 1–20 carbons, substituted or unsubstituted aryl of 6–10 carbons, substituted or unsubstituted araliphatic of 7–22 carbons or a substituted or unsubstituted alicyclic group of 5–12 carbons which may optionally contain —N($R^9$)— as a group member and $R^4$ and $R^5$ may optionally be linked together to form an alicyclic group of 5–7 atoms or may be linked together through a heteroatom —N($R^{10}$)— or —O— to form a heterocyclic ring of 5–7 atoms. Preferably, $R^4$, $R^5$ and $R^7$ are independently hydrogen, substituted or unsubstituted alkyl of 1–4 carbons, substituted or unsubstituted cyclohexyl, substituted or unsubstituted benzyl or substituted or unsubstituted phenyl.

$R^6$ is substituted or unsubstituted aliphatic of 1–20 carbons, substituted or unsubstituted aryl of 6–10 carbons, substituted or unsubstituted araliphatic of 7–22 carbons or a substituted or unsubstituted alicyclic group of 5–12 carbons which may optionally contain —N(R$^9$)— as a group member. Preferably, $R^6$ is substituted or unsubstituted alkyl of 1–6 carbons, substituted or unsubstituted aralkyl of 7 to 10 carbons or substituted or unsubstituted phenyl.

$R^8$ is hydroxy, —O$^\ominus$, halogen, —NH$_2$, —NHNH$_2$ or the residue from a substituted or unsubstituted, monofunctional or polyfunctional alcohol, amine, mercaptan or hydrazine group or molecular mixture thereof, wherein hydroxy-containing and amine-containing polymers may be backbone, pendant or terminally functionalized.

$R^9$ and $R^{10}$ are independently hydrogen or substituted or unsubstituted alkyl of 1–4 carbons.

s is an integer of 1–100.

A is an anion chloride, bromide, sulfate, acid sulfate, sulfite, acid sulfite, p-toluenesulfonate, phenylsulfonate, methylsulfonate, phosphate, acid phosphate, carboxylate from any carboxylic acid or $R^8$ when $R^8$ is —O$^\ominus$.

Substituents for the alkyl, aliphatic, aryl, araliphatic, alicyclic, aliphatic acyl, aryl acyl or araliphatic acyl radicals, $R^1$, $R^2$, $R^3$, $R^4$, $R^5$, $R^6$, $R^7$, $R^8$, $R^9$ and $R^{10}$ independently are one or more of aliphatic of 1–8 carbons, alkoxy of 1–4 carbons, alkanoyl of 1–12 carbons, alkanoyloxy of 1–12 carbons, alkoxycarbonyl of 2–5 carbons, arylcarbonyl of 7–11 carbons, acryloyloxy, methacryloyloxy, aryloxy of 6–10 carbons, aralkyl of 7–10 carbons, aryloxycarbonyl of 7–11 carbons, aryl of 6–10 carbons, amino, hydroxy, carboxy, nitrile, chloro, bromo, epoxy, vinyl, alkyl mercapto of 1–4 carbons, benzoyloxy, aryl mercapto of 6–10 carbons, alkylamino of 1–4 carbons, dialkylamino of 2–8 carbons, arylamino of 6–10 carbons, aryl alkyl amino of 7–10 carbons or trialkoxysilyl of 3–9 carbons.

DETAILED DESCRIPTION OF THE PREFERRED EMBODIMENTS

General Formula

The compounds of this invention are characterized by the presence of at least one hindered amine group attached to the nitrogen of an imide which is also attached to an aromatic group, which also contains a carboxy group or a derivative thereof having the general formula I:

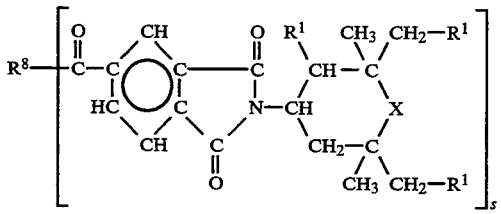

wherein $R^1$, $R^8$, s and X are as previously defined.

Generic Group Examples

As an alkyl of 1–4 carbons, and $R^1$, $R^9$ and $R^{10}$ are independently, for example, methyl, ethyl, propyl, isopropyl, butyl and sec-butyl.

As a substituted or unsubstituted aliphatic radical of 1–20 carbons, $R^3$, $R^4$, $R^5$, $R^6$ and $R^7$ are independently, for example, methyl, ethyl, n-propyl, isopropyl, butyl, allyl, n-pentyl, hexyl, heptyl, 2-bromoethyl, octyl, nonyl, decyl, propargyl, octadecyl, dodecyl, isododecyl, tetradecyl, methallyl, 2-hexenyl, 10-undecenyl, 2-dodecenyl, 2-acetoxyethyl, 2-hydroxyethyl, 2-butenyl, 2-hydroxyhexadecyl, 2-hydroxypropyl, 2-hexenyl, 10-undecenyl, 2-dodecenyl, 2-hydroxydodecyl, 2-hydroxy-5-hexenyl, 2-hydroxyhexyl, 2-hydroxydecyl, 2-hydroxyoctadecyl, 2-hydroxy-3-(methacryloyloxy)propyl, 2-hydroxy-3-(acryloyloxy)propyl, 2-hydroxy-3-phenoxypropyl, 2-hydroxy-3-(4-methoxyphenoxy)propyl, 3-(trimethoxysilyl)propyl, 2-hydroxy-3-methoxypropyl, 2-hydroxy-3-(cyclohexyloxy)propyl, 2-hydroxy-3-(benzyloxy)propyl, 2-hydroxy-3-(benzoyloxy)propyl, 2-hydroxy-3-dodecyloxypropyl, 2-hydroxybutyl, 1-methyl-2-hydroxypropyl, cyanomethyl, 2,3-epoxypropyl, 2-(dimethylamino)ethyl or propargyl.

As a substituted or unsubstituted aryl radical of 6–10 carbons, $R^4$, $R^5$, $R^6$ and $R^7$ are independently, for example, phenyl, tolyl, 4-butoxyphenyl, 2-methoxyphenyl, 4-chlorophenyl, isopropylphenyl, isopropenylphenyl, anisyl, trimethylphenyl, 4-n-octylphenyl, 3,5-di(t-butyl)-4-hydroxyphenyl, 3,5-di(t-amyl)-4-hydroxyphenyl, 4-vinylphenyl, 3-(t-butyl)-5-methyl-4-hydroxyphenyl, naphthyl, 3-methyl-5-t-butyl-4-hydroxyphenyl, 3,4,5-trimethoxyphenyl or 4-dimethylaminophenyl.

As a substituted or unsubstituted araliphatic radical of 7–22 carbons, $R^3$, $R^4$, $R^5$, $R^6$ and $R^7$ are independently, for example, benzyl, 3-methylbenzyl, 4-t-butylbenzyl, cinnamyl, 3,5-di-t-butyl-4-hydroxybenzyl, 2-phenoxyethyl, 2-hydroxy-2-phenylethyl, 2-phenylethyl, 1-methyl-1-phenylethyl, 3-phenylpropyl, trimethylbenzyl, 4-octyloxybenzyl, naphthylmethyl, (4-dodecylphenyl)methyl, 2-(3,5-di-t-butyl-4-hydroxyphenyl)ethyl, 2-(3,5-di-t-amyl-4 -hydroxyphenyl)ethyl or 2-(3-t-butyl-5-methyl-4-hydroxyphenyl)ethyl.

As a substituted or unsubstituted alicyclic group of 5–12 carbons which may optionally contain —N(R$^9$)— as a ring member, $R^4$, $R^5$, $R^6$ and $R^7$ are, independently for example, cyclohexyl, trimethylcyclohexyl, cyclooctyl, cyclododecyl, 4-t-butylcyclohexyl, 2-hydroxycyclododecyl, 3-cyclohexenyl, 2-hydroxycyclohexyl, 2-hydroxycyclopentyl, cyclododecyl, 4-octylcyclohexyl, 2,2,6,6-tetramethyl-4-piperidinyl, 2,6-diethyl-2,3,6-trimethyl-4-piperidinyl, 1,2,2,6,6-pentamethyl-4-piperidinyl, 1-(2-hydroxyethyl)-2,2,6,6-tetramethyl-4-piperidinyl or 2-methyl-4-octylcyclohexyl.

As a substituted or unsubstituted aliphatic acyl radical of 1–20 carbons, alicyclic acyl radical of 6–14 carbons, aryl acyl radical of 7–11 carbons or araliphatic acyl radical of 7–22 carbons, $R^2$ is, for example, formyl, acetyl, chloroacetyl, acryloyl, methacryloyl, propionyl, 2-methylpropionyl, 3-phenylpropionyl, crotonoyl, butyryl, octanoyl, dodecanoyl, caproyl, capryloyl, lauroyl, stearoyl, octadecanoyl, cyclohexylcarbonyl, 4-t-butylcyclohexylcarbonyl, 3-cyclohexenyl-1-carbonyl, cyclododecylcarbonyl, 4-octylcyclohexylcarbonyl, 2-ethoxy-2-oxoacetyl, 2-methoxy-2-oxoacetyl, cinnamoyl, dihydrocinnamoyl, 2-methyl-4-octylcyclohexylcarbonyl, 4-ethoxybenzoyl, benzoyl, chlorobenzoyl, isopropylbenzoyl, 2,4-dichlorobenzoyl, toluoyl, anisoyl, 3-butoxybenzoyl, 2-hydroxybenzoyl, 3,5-di-t-butyl-4-hydroxybenzoyl, 3-(3,5-di-t-butyl-4-hydroxyphenyl)propionyl, 3-methyl-5-t-butyl-4-hydroxybenzoyl, 3,4,5-trimethoxybenzoyl, 4-(dimethylamino)benzoyl, cyclohexyl-1-carbonyl, phenylacetyl, phenethyl, 1- or 2-naphthoyl or decahydronaphthoyl.

As —C(=O)—N(R⁴)(R⁵), wherein R⁴ and R⁵ are linked together to form an alicyclic group of 5–7 atoms or are linked together through a heteroatom —N(R¹⁰)— or —O— to form a heterocyclic group of 5–7 atoms, R² is, for example, piperidin-1-ylcarbonyl, 2,2,6,6-tetramethyl-4-piperidinylcarbonyl, piperazine-1-carbonyl, 4-methylpiperazine-1-carbonyl or morpholine-1-carbonyl.

As a substituted or unsubstituted alkoxyalkyl of 2–21 carbons, the alkyl part of R³ contains, for example, 1–3 carbons and the alkoxy part contains, for example, 1–18 carbons, as in, for example, methoxymethyl, ethoxymethyl, 2-hydroxy-3-isopropoxypropyl, 2-methoxyethyl, 2-ethoxyethyl, 2-n-butoxyethyl, 2-hydroxy-3-(2-ethylhexyloxy)propyl, 3-n-butoxypropyl, 2-octoxyethyl or 2-octdecyloxyethyl.

R⁸ defines a derivative of the aromatic carboxylic acid group of general formula I and as such, must contain at least one oxygen, nitrogen, sulfur or halogen atom capable of bonding to the aryl acyl group. When attached by an oxygen, nitrogen or sulfur of R⁸, the invention comprises a compound containing one or more groups having the general formula I shown above incorporated as one or more ester, amide, thioester or hydrazide groups. Mixtures of ester, amide and thioester are derived from substituted or unsubstituted, monofunctional or polyfunctional alcohol, amine, mercaptan or hydrazine groups or molecular mixture thereof, including hydroxy-containing and amine-containing polymers which may be backbone, pendant or terminally functionalized.

As a halogen, R⁸ is, for example, chlorine or bromine; preferably chlorine.

As the residue from a substituted or unsubstituted, monofunctional or polyfunctional alcohol, amine, mercaptan or hydrazine or molecular mixture thereof, R⁸ is, for example, any of the following:

When s is 1, R⁸ is 1-morpholinyl, 1-piperidinyl, 1-pyrrolidinyl or R¹¹—Y—.

Y is —O—, —N(R¹²)—, —S—, —C(=O)—NH—NH—, —NH—NH—, —NH—C(=O)—NH—NH—, —O—C(=O)—NH—NH—, —NH—C(=O)—C(=O)—NH—NH— or —O—C(=O)—C(=O)—NH—NH—.

R¹¹ is, for example, hydrogen, substituted or unsubstituted aliphatic of 1–20 carbons, substituted or unsubstituted aryl of 6–10 carbons, substituted or unsubstituted araliphatic of 7–22 carbons, a substituted or unsubstituted alicyclic group of 5–12 carbons which may optionally contain —N(R¹³)— as a group member, trialkylsilylalkyl of 5–20 carbons, alkyldiarylsilylalkyl of 15–20 carbons, alkoxyalkyl of 3–20 carbons, substituted or unsubstituted 3-(2H-benzotriazol-2-yl)-2-hydroxybenzyl, substituted or unsubstituted 4-benzoyl-3-hydroxyphenoxymethyl, substituted or unsubstituted 4-benzoyl-3-hydroxyphenoxyethyl, trialkoxysilylpropyl of 4–15 carbons, substituted or unsubstituted 4-[2,2,-di(methoxycarbonyl)ethenyl]phenyl or polyalkyl having a general formula CH₃—(CH₂)ₖ— in which c is an integer of 25–50.

R¹² is, for example, hydrogen, substituted or unsubstituted aliphatic of 1–20 carbons, substituted or unsubstituted aryl of 6–10 carbons, substituted or unsubstituted araliphatic of 7–22 carbons or a substituted or unsubstituted alicyclic group of 5–12 carbons which may optionally contain —N(R¹⁴)— as a group member.

R¹³ and R¹⁴ are independently, for example, hydroxy, substituted or unsubstituted aliphatic acyl of 1–20 carbons, substituted or unsubstituted alicyclic acyl of 6–14 carbons, substituted or unsubstituted aryl acyl of 7–11 carbons, substituted or unsubstituted araliphatic acyl of 7–22 carbons, —C(=O)—N(R⁴)(R⁵), —C(=O)—O—R⁶, substituted or unsubstituted aliphatic of 1–20 carbons, substituted or unsubstituted araliphatic radical of 7–22 carbons, alkoxyalkyl of 2–21 carbons and —CH₂—C(=O)—O—R⁷.

When s is 1 or more, R⁸ is any of the following polyvalent groups (i)–(xii) with the understanding that any valence not satisfied by attachment to the acyl group shown in the general formula I is satisfied by a group R¹⁵.

R¹⁵ is hydrogen, substituted or unsubstituted aliphatic of 1–20 carbons, substituted or unsubstituted aryl of 6–10 carbons, substituted or unsubstituted araliphatic of 7–22 carbons and substituted or unsubstituted alicyclic of 5–12 carbons, substituted or unsubstituted aliphatic acyl of 1–20 carbons, substituted or unsubstituted alicyclic acyl of 6–14 carbons, substituted or unsubstituted aryl acyl of 7–11 carbons or substituted or unsubstituted araliphatic acyl of 7–22 carbons.

(i) R⁸ is 1,4-piperazindiyl.
(ii) R⁸ is —Y—R¹⁶—Y— wherein Y is as previously defined.

R¹⁶ is a substituted or unsubstituted aliphatic diradical of 2–20 carbons, substituted or unsubstituted alicyclic diradical of 5–20 carbons, substituted or unsubstituted aryl diradical of 6–10 carbons, substituted or unsubstituted araliphatic diradical of 7–22 carbons, where the aliphatic, alicyclic and araliphatic diradicals may contain heteroatoms nitrogen, sulfur or oxygen, 4,4'-oxybis(phenylene)-diyl, 1,2-phenylenebis(oxyalkyl) of 10–14 carbons, 1,4-phenylenebis(oxyalkyl) of 10–14 carbons, oxybis(dimethylsilylpropyl), 4,4'-biphenyldiyl, 2,2-propane-bis(phenylene)-p,p'-diyl, diphenylsulfone-4,4'-diyl,
poly(alkoxy)dialkyl having a general formula

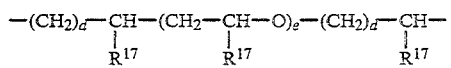

in which R¹⁷ is hydrogen, substituted or unsubstituted aliphatic of 1–20 carbons or substituted or unsubstituted araliphatic of 7–10 carbons and d is an integer of 1 or 2 and e is an integer of 0–350,
polycarbonate diradicals having a general formula

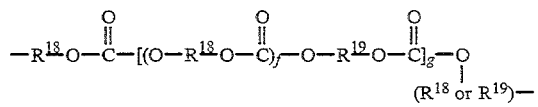

in which f and g are independently integers of 1–5 and R¹⁸ and R¹⁹ are independently a substituted or unsubstituted aliphatic diradical of 2–20 carbons, substituted or unsubstituted alicyclic diradical of 5–12 carbons, substituted or unsubstituted aryl diradical of 6–10 carbons or substituted or unsubstituted araliphatic diradical of 7–22 carbons,
diester and polyester diradicals having a general formula

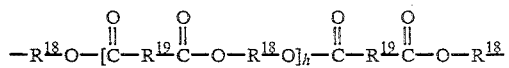

in which h is an integer of 0 to 10, unsaturated polyolefin diradicals having a molecular weight of from about 2000 to about 3500,
poly(mercaptoether) diradicals

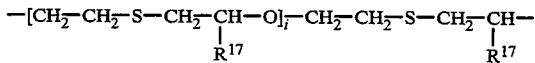

in which i is an integer of 2–12,
unsaturated copolymer diradicals having a general formula

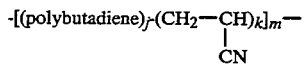

in which m is an integer of 5–10 and j and k are component fractions, k is about 0.1 to about 0.3 and j is 1-k,
poly(organosiloxane) diradicals having a general formula

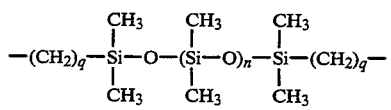

in which n is an integer of 5–3000 and q is an integer of 3 or 4 or
polyester diradicals having a general formula

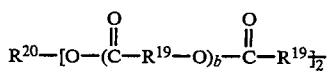

in which b is an integer of 0–10 and may be different for each of the two repeating groups, and $R^{20}$ is an aliphatic diradical of 2 to 4 carbons.

Non-limiting examples of $R^{16}$ are 1,2-ethanediyl, 1,2-propanediyl, 1,3-propanediyl, 1,4-butanediyl, 1,18-octadecanediyl, 2,2-dimethyl-1,3-propane-diyl, 2-methylpentane-2,4-diyl, 1,10-decanediyl, 1,12-dodecanediyl, 3-oxapentane-1,5-diyl, 4-oxaheptane-1,7-diyl, 3,6-dioxaoctane-1,8-diyl, 4,9-dioxadodecane-1,12-diyl, 4-methyl-4-azaheptane-1,4-diyl, 3,6-diaza-3,6-dimethyl-1,8-octanediyl, 3-methyl-3-azapentane-1,5-diyl, tricyclo[5.2.1.0$^{1,5}$]decane-3,7-diylbis(methyl), 1,2-cyclohexanediyl, 1,4-cyclohexanediyl, 1,2-ethenediyl, 1,2-propenediyl, 1-chloro-1,2-ethenediyl, cyclohexane-1,4-bis(methyl), 1-phenyl-1,2-ethenediyl, 1,3-hexanediyl, 1,2-cyclohexanediyl, 1,2-phenylene, 4-methyl-4-cyclohexene-1,2-diyl, 4-cyclohexene-1,2-diyl, 4-methylcyclohexane-1,2-diyl, 4-carboxy-1,2-phenylene, 4-methoxycarbonyl-1,2-phenylene, propane-2,2-bis[4-cyclohexyl], propane-2,2-bis[4-phenyl], 3-oxapentane-1,5-diyl, methylenebis[4-cyclohexyl], 1,2-, 1,3-, or 1,4-phenylene, 1,2-, 1,3-, or 1,4-phenylenebis(methyl), biphenyl-4,4'-diyl, biphenyl-3,3'-diyl, biphenyl-3,4'-diyl, methylenebis[phenylene], octadecane-1,2-diyl, octane-2,4-diyl, 3-butoxypropane-1,2 -diyl, 1-phenylpropane-1,2-diyl, 3-phenoxypropane-1,2-diyl, 3-(4-t-butylphenoxy)propane-1,2-diyl, 3-(3-pentadecylphenoxy)propane-1,2-diyl, 3-allyloxypropane-1,2-diyl, 1-methyl-4-isopropylidenecyclohexane-1,2-diyl, 3-(alkyl(C$_{11-13}$)carbonyloxy)propane-1,2-diyl, 4-vinylcyclohexane-1,2-diyl, 2,2,6-trimethylbiciclo[3.1.1]heptane-2,3-diyl, 3-(methacryloxy)propane-1,2-diyl or polybutadiene-alpha, omega-diyl.

(iii) $R^8$ is 4-aza-1,7-dioxaheptane-1,4,7-triyl.
(iv) $R^8$ is

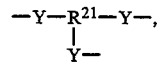

wherein Y is as previously defined, and
$R^{21}$ is a substituted or unsubstituted aliphatic triradical of 3–20 carbons, substituted or unsubstituted aryl triradical of 6–13 carbons or substituted or unsubstituted araliphatic triradical of 7–22 carbons, where the aliphatic, alicyclic and araliphatic triradicals may contain heteroatoms nitrogen, sulfur or oxygen, with the proviso that the heteroatoms are separated from each other and Y by at least one carbon atom, or a polyester triradical having a general formula

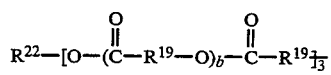

in which b is as previously defined and may be different for each of the three repeating groups, where $R^{22}$ is an aliphatic triradical of 3 to 8 carbons.

Non-limiting examples of $R^{21}$ are propane-1,2,3-triyl, pentane-1,3,5-triyl, nitrillotriethyl, —CH$_2$—CH$_2$—CH$_2$—N(CH$_2$—CH$_2$—)$_2$, 1,3,5-triazine-2,4,6-triyl,

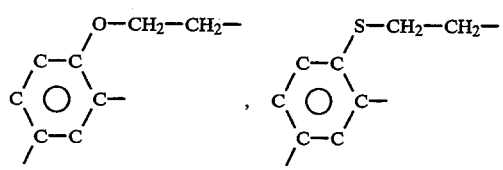

or $R^{22}$—[O—(C(=O)—(CH$_2$)$_5$—O)$_b$]$_3$—.

(v) $R^8$ is

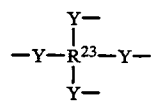

wherein Y is as previously defined, and $R^{23}$ is a substituted or unsubstituted aliphatic tetraradical of 4–20 carbons, substituted or unsubstituted alicyclic tetraradical of 6–16 carbons, substituted or unsubstituted aryl tetraradical of 6–14 carbons or substituted or unsubstituted araliphatic tetraradical of 7–22 carbons.

Non-limiting examples of $R^{23}$ are oxybis(cyclopentane-2,3-diyl), 4,7,10-trioxatetradecane-1,2,13,14-tetrayl, 4,9-dioxadodecane-1,2,11,12-tetrayl, butane-1,2,3,4-tetrayl,

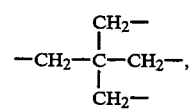

-continued

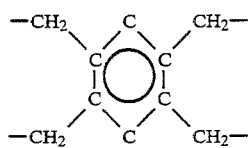

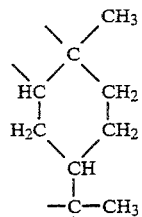

or

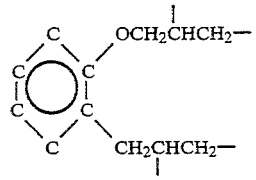

(vi) $R^8$ is

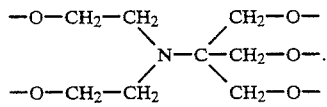

(vii) $R^8$ is

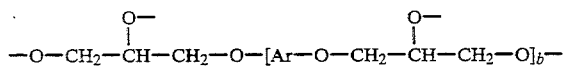

wherein
Ar is

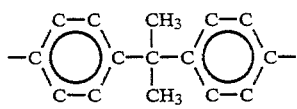

and b is as previously defined.

(viii) $R^8$ is

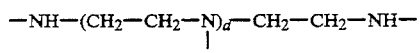

wherein d is as previously defined.

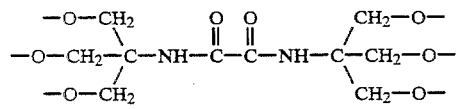

(x) $R^8$ is

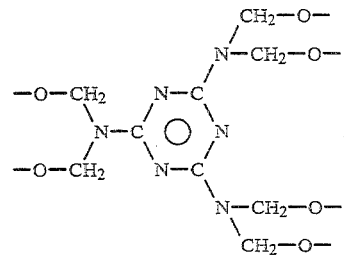

(xi) $R^8$ is

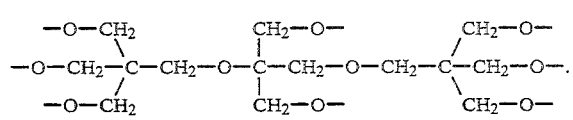

(xii) $R^8$ is a polymeric or copolymeric radical containing recurring units

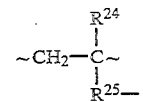

wherein $R^{24}$ is hydrogen alkyl of 1–4 carbons or phenyl, $R^{25}$ is —O—, —N($R^{26}$)—, —CH$_2$—O—, —C(=O)—O—CH$_2$—CH(OH)—CH$_2$—O—, —C(=O)—O—CH$_2$—CH$_2$—O— or —C(=O)—O—CH$_2$—CH$_2$—O—, $R^{26}$ is hydrogen, substituted or unsubstituted aliphatic of 1–20 carbons, substituted or unsubstituted aryl of 6–10 carbons, substituted or unsubstituted araliphatic of 7–22 carbons or substituted or unsubstituted alicyclic of 5–12 carbons, and the symbol ~ represents the polymer or copolymer backbone in which the units recur.

As the anion from a carboxylic acid, A is, for example, oxalate, benzoate, formate, acetate, 4-methylbenzoate, isobutyrate, propionate, succinate, or terephthalate.

The substituents for $R^{11}$, $R^{12}$, $R^{13}$, $R^{14}$, $R^{15}$, $R^{16}$, $R^{17}$, $R^{18}$, $R^{19}$, $R^{21}$, $R^{23}$ and $R^{26}$ are independently those set forth above for $R^8$.

List of Illustrative Compounds

In the following non-limiting list of illustrative compounds of the present invention, the N-(hindered amine)-phthalimide group appears as both a substituent and as a parent group. The substituent nomenclature used is N-(hindered amine)phthalimide-4-carbonyl-. When named as a molecular parent, the name follows accepted convention.

1. N-[1-(phenoxycarbonyl)-2,2,6,6-tetramethyl-4-piperidinyl]-4-(methoxycarbonyl)phthalimide
2. N-(2,2,6,6-tetramethyl-4-piperidinyl)-4-(bromocarbonyl)phthalimide, hydrobromide salt
3. N-(2,2,6,6-tetramethyl-4-piperidinyl)-4-(carboxy)phthalimide, p-toluenesulfonate salt
4. N-(2,2,6,6-tetramethyl-4-piperidinyl)-4-[(3,5-di-t-butyl-4-hydroxybenzyloxy)carbonyl]phthalimide
5. N-(2,2,6,6-tetramethyl-4-piperidinyl)-4-{[2-hydroxy-3-(2H-benzotriazol-2-yl)-5-methylbenzyl]aminocarbonyl}phthalimide
6. N-(2,2,6,6-tetramethyl-4-piperidinyl)-4-[5-(4-benzoyl-3-hydroxyphenoxy)-1,4-dioxo-2,3-diazapentyl]phthalimide 7. N-[1-(2,3-epoxy)propyl-2,2,6,6-tetramethyl-4-piperidinyl]-4-(methoxycarbonyl)phthalimide
8. N-[1-(2,3-epoxy)propyl-2,2,6,6-tetramethyl-4-piperidinyl]-4-[2,3-(epoxy)propoxycarbonyl]phthalimide
9. N-(2,2,6,6-tetramethyl-4-piperidinyl)-4-{[3-(methacryloxy)-2-hydroxypropoxy]carbonyl}phthalimide
10. N-(2,2,6,6-tetramethyl-4-piperidinyl)-4-{[3-(allyloxy)-2-hydroxypropoxy]carbonyl}phthalimide
11. N-(2,2,6,6-tetramethyl-4-piperidinyl)-4-{[3-(n-butoxy)-2-hydroxypropoxy]carbonyl}phthalimide
12. N-(2,2,6,6-tetramethyl-4-piperidinyl)-4-{[2-hydroxy-4-vinylcyclohexyloxy]carbonyl}phthalimide
13. N-[1-(2-hydroxy-2-phenylethyl)-2,2,6,6-tetramethyl-4-piperidinyl]-4-{[2-phenyl-2-hydroxyethoxy]carbonyl}phthalimide
14. N-(2,2,6,6-tetramethyl-4-piperidinyl)-4-{[2-hydroxy-2-methyl-5-(isopropylidene)cyclohexyloxy]carbonyl}phthalimide
15. N-(2,2,6,6-tetramethyl-4-piperidinyl)-4-{[3-phenoxy-2-hydroxypropoxy]carbonyl}phthalimide
16. N-(2,2,6,6-tetramethyl-4-piperidinyl)-4-{[3-(4-butylphenoxy)-2-hydroxypropoxy]carbonyl}phthalimide
17. N-(2,2,6,6-tetramethyl-4-piperidinyl)-4-{[1,5,5-trimethyl-1-hydroxybicyclo(3.1.1)heptane-2-yloxy]carbonyl}phthalimide
18. N-(2,2,6,6-tetramethyl-4-piperidinyl)-4-{[3-(3-pentadecylphenoxy)-2-hydroxypropoxy]carbonyl}phthalimide
19. N-(2,2,6,6-tetramethyl-4-piperidinyl)-4-{[3-(t-alkyl($C_8$-$C_{10}$)carbonyloxy)-2-hydroxypropoxy]carbonyl}phthalimide
20. 4,4'-(4,8-dihydroxy-2,6,10-trioxa-1,11-dioxoundecane-1,11-diyl)-bis[N-(2,2,6,6-tetramethyl-4-piperidinyl)phthalimide]
21. 1,2-di{2-hydroxy-4-oxa-4-[N-(2,2,6,6-tetramethyl-4-piperidinyl)phthalimide-4-carbonyl]butyl}benzene
22. 1,2-di{2-hydroxy-4-oxa-4-[N-(2,2,6,6-tetramethyl-4-piperidinyl)phthalimide-4-carbonyl]butoxy}benzene
23. 4,4'-(4,14-dihydroxy-2,6,9,12,16-pentaoxa-1,17-dioxoheptadecane-1,17-diyl)-bis[N-(2,2,6,6-tetramethyl-4-piperidinyl)phthalimide]
24. 4,4'-(4,5-dihydroxy-2,7-dioxa-1,8-dioxooctane-1,8-diyl)-bis[N-(2,2,6,6-tetramethyl-4-piperidinyl)phthalimide]
25. 4,4'-(4,6-dihydroxy-4,6-dimethyl-2,8-dioxa-1,9-dioxononane-1,9-diyl)-bis[N-(2,2,6,6-tetramethyl-4-piperidinyl)phthalimide]
26. N-(2,2,6,6-tetramethyl-4-piperidinyl)-4-{[(3,5-di(n-butylmercapto)-2,4,6-triazin-1-yl]aminocarbonyl}phthalimide
27. N-(2,2,6,6-tetramethyl-4-piperidinyl)-4-{[3,5-diamino-2,4,6-triazin-1-yl]aminocarbonyl}phthalimide
28. N-(2,2,6,6-tetramethyl-4-piperidinyl)-4-{[3,5-dimethoxy-2,4,6-triazin-1-yl]aminocarbonyl}phthalimide
29. N-(2,2,6,6-tetramethyl-4-piperidinyl)-4-[(2-bromoethoxy)carbonyl]phthalimide
30. 6-(n-butylmercapto)-2,4-di[N-(2,2,6,6-tetramethyl-4-piperidinyl)phthalimide-4-carbonylamino]-1,3,5-triazine
31. N-[1-(dibutylaminocarbonyl)-2,2,6,6-tetramethyl-4-piperidinyl]-4-[2-(n-butoxy)ethoxycarbonyl]phthalimide
32. N-(2,2,6,6-tetramethyl-4-piperidinyl)-[1-methyl-2-(ethoxycarbonyl)ethoxycarbonyl]phthalimide
33. N-(2,2,6,6-tetramethyl-4-piperidinyl)-4-[6-(2,2,6,6-tetramethyl-4-piperidinyl)-2,3,6-triaza-1,4,5-trioxohexyl]phthalimide
34. N-(2,2,6,6-tetramethyl-4-piperidinyl)-4-[6-(3,5-di-t-butyl-4-hydroxyphenyl)-2,3-diaza-1,4-dioxohexyl]phthalimide
35. N-(2,2,6,6-tetramethyl-4-piperidinyl)-4-[6-(n-hexylmercapto)-2,3-diaza-1,4-dioxohexyl]phthalimide
36. N-(2,2,6,6-tetramethyl-4-piperidinyl)-4-[7-(2,2,6,6-tetramethyl-4-piperidinyl)-2,3,7-triaza-1,4-dioxoheptyl]phthalimide
37. 1,4-di[N-(2,6-dimethyl-2,6-dipropyl-3-ethyl-4-piperidinyl)phthalimide-4-carbonyl]piperazine
38. 1,4-di[N-(2,2,6,6-tetramethyl-4-piperidinyl)phthalimide-4-carbonyloxy]benzene
39. N-{1-[(butoxycarbonyl)methyl]-2,2,6,6-tetramethyl-4-piperidinyl)-4-(butoxycarbonyl)phthalimide
40. 2,2-di{4-[N-(2,2,6,6-tetramethyl-4-piperidinyl)phthalimide-4-carbonyloxy]phenyl}propane
41. 4,4'-(4-hydroxy-2,6-dioxa-1,7-dioxoheptane-1,7-diyl)-bis[N-(2,2,6,6-tetramethyl-4-piperidinyl)phthalimide]
42. 4,4'-(2,5,8-trioxa-1,9-dioxononane-1,9-diyl)-bis[N-(2,2,6,6-tetramethyl-4-piperidinyl)phthalimide]
43. N-(2,2,6,6-tetramethyl-4-piperidinyl)-4-{[3-(trimethoxysilyl)propyl]aminocarbonyl}phthalimide
44. N-(1-benzyl-2,2,6,6-tetramethyl-4-piperidinyl)-4-{[2-(dimethylamino)ethyl]aminocarbonyl}phthalimide
45. 1,4-di[N-(2,6-diethyl-2,6-dimethyl-3-methyl-4-piperidinyl)phthalimide-4-carbonylamino]benzene
46. 4,4'-[4,4-di(hydroxymethyl)-2,6-dioxa-1,7-dioxoheptane-1,7-diyl)]-bis[N-(2,2,6,6-tetramethyl-4-piperidinyl)phthalimide]
47. 4,4'-{4,4-di{[N-(2,2,6,6-tetramethyl-4-piperidinyl)phthalimide-4-carbonyloxy]methyl}-2,6-dioxa-1,7-dioxoheptane-1,7-diyl}-bis[N-2,2,6,6-tetramethyl-4-piperidinyl)phthalimide]
48. N-(2,2,6,6-tetramethyl-4-piperidinyl)-4-carboxyphthalimide, ester with poly(caprolactone)-triol, 3:1
49. N-(2,2,6,6-tetramethyl-4-piperidinyl)-4-carboxyphthalimide, ester with poly(propyleneoxide)-diol, 2:1
50. N-(2,2,6,6-tetramethyl-4-piperidinyl)-4-carboxyphthalimide, product with epoxy resin (Bisphenol-A/epichlorohydrin)
51. 1,4-di{[N-(2,2,6,6-tetramethyl-4-piperidinyl)phthalimide-4-carbonyloxy]methyl}cyclohexane
52. N-(2,2,6,6-tetramethyl-4-piperidinyl)-4-{[2-(4-benzoyl-3-hydroxyphenoxy)ethoxy}carbonyl]phthalimide
53. 7-[N-(2,2,6,6-tetramethyl-4-piperidinyl)phthalimide-4-carbonyloxy]-3-{[N-(2,2,6,6-tetramethyl-4-piperidinyl)phthalimide-4-carbonyloxy]methyl}tricyclo(5.2.1.0$^{1,5}$)decane
54. 4,4'-{4-[N-(2,2,6,6-tetramethyl-4-piperidinyl)phthalimide-4-carbonylmercapto]-2,6-dioxa-1,7-dioxoheptane-1,7-diyl}-bis[N-(2,2,6,6-tetramethyl-4-piperidinyl)phthalimide]
55. 1,3-di[N-(2,2,6,6-tetramethyl-4-piperidinyl)phthalimide-4-carbonylamino]-4-{6-[N-(2,2,6,6-tetramethyl-4-piperidinyl)phthalimide-4-carbonyl]-5-oxa-1-thiapentyl}benzene
56. N-(1,2,2,6,6-pentamethyl-4-piperidinyl)-4-{[(3-benzoyloxy)phenoxy]carbonyl}phthalimide
57. N-[1-(2-hydroxyethyl)-2,2,6,6-tetramethyl-4-piperidinyl]-4-{[2-(acryloyloxy)ethoxy]-carbonyl}phthalimide 58. N-(2,2,6,6-tetramethyl-4-piperidinyl)-4-[(2-aminoethyl)aminocarbonyl]phthalimide
59. methyl methacrylate/glycidyl methacrylate/N-(2,2,6,6-tetramethyl-4-piperidinyl)-4-{[3-(methacryloyloxy)-2-hydroxypropoxy]carbonyl}phthalimide terpolymer
60. N-(2,2,6,6-tetramethyl-4-piperidinyl)-4-carboxyphthalimide, ester with poly[oxycarbonyloxy-1,4-phenylene(1-methylethylidene)-1,4-phenylene], 2:1
61. N-(2,2,6,6-tetramethyl-4-piperidinyl)-4-(2-hydroxypropoxycarbonyl)phthalimide
62. N-(2,2,6,6-tetramethyl-4-piperidinyl)-4-{[2-(3,3-diphenyl-2-cyanoacryloyloxy)ethoxy]carbonyl}phthalimide
63. 2-{N-[methoxymethyl]-N-[n-(2,2,6,6-tetramethyl-4-piperidinyl)phthalimide-4-carbonyloxymethyl]amino}-4,6-di[N,N-di(methoxymethyl)amino]-1,3,5-triazine
64. 4,4'-(2,7-dioxa-1,8-dioxo-4-octene-1,8-diyl)bis[N-(1-benzoyl-2,2,6,6-tetramethyl-4-piperidinyl)phthalimide]
65. 2,4-di[N-(2,2,6,6-tetramethyl-4-piperidinyl)phthalimide-4-carbonylamino]-1-{2-[N-(2,2,6,6-tetramethyl-4-piperidinyl)phthalimide-4-carbonyloxy]ethoxy}benzene
66. 4,4'-(ethane-1,2-diyl) bis{N-[1-[(cyclohexyloxycarbonyl)methyl]-2,2,6,6-tetramethyl-4-piperidinyl]phthalimide]
67. tri{[N-(2,2,6,6-tetramethyl-4-piperidinyl)phthalimide-4-carbonyloxy]ethyl}amine
68. 4-(2-phenoxyethoxy)carbonyl-N-[1-(2-acetoxyethyl)-2,2,6,6-tetramethyl-4-piperidinyl]phthalimide
69. alpha,omega-di[N-(2,6-diethyl-2,6-dimethyl-3-methyl-4-piperidinyl)phthalimide-4-carbonyloxy]-polybutadiene
70. N-(1-butyl-2,2,6,6-tetramethyl-4-piperidinyl)-4-(N-methyl-N-phenylaminocarbonyl)phthalimide, trihydrogen phosphate salt

Utility

The novel stabilizers of this invention are effective additives for the stabilization of polymeric compositions which are normally subject to thermal, oxidative or actinic light degradation. At times it may be beneficial to add extraneous additives which will act as synergists with the hindered amine light stabilizing group.

Thus, another aspect of the present invention relates to a process of stabilizing a synthetic or natural polymer composition against the degradative effects of heat or light by mixing with the polymer composition a compound of general formula I in an amount effective to stabilize the polymer composition against the degradative effects of heat or light.

Yet another aspect of this invention concerns a polymeric composition stabilized against the degradative effects of heat or light comprising a synthetic or natural polymer mixed with a compound of general formula I in an amount effective to stabilize the polymer against the degradative effects of heat or light.

The novel stabilizers of this invention can be blended with various polymeric compositions in high concentrations to form masterbatches which can then be blended with additional polymer either of the same or different type.

The amount of stabilizer used to stabilize the polymeric composition will depend on the particular polymer system to be stabilized, the degree of stabilization desired and the optional presence of other stabilizers in the composition. Normally it is advisable to have about 0.01 to about 5% by weight of the 2,2,6,6,-tetraalkylpiperidine moiety of the compound of this invention present in the polymeric composition. An advantageous range is from about 0.05 to about 2% by weight of the 2,2,6,6-tetraalkylpiperidine portion of the molecule in the final composition. In most cases about 0.1% to about 1% by weight is sufficient.

Non-limiting examples of polymers and copolymers which may be stabilized by the compounds of the present invention include:

1. Polyolefins, such as high, low and linear low density polyethylenes, which may be optionally crosslinked, polypropylene, polyisobutylene, poly(methylbutene-1), polyacetylene and, in general, polyolefins derived from monomers having from 2 to about 10 carbon atoms, and mixtures thereof.

2. Polyolefins derived from diolefins, such as polybutadiene and polyisoprene.

3. Copolymers of monoolefins or diolefins, such as ethylene-propylene, propylene-butene-1, propylene-isobutylene and ethylene-butene-1 copolymer.

4. Terpolymers of ethylene and propylene with dienes (EPDM), such as butadiene, hexadiene, dicyclopentadiene and ethylidene norbornene.

5. Copolymers of alpha-olefins with acrylic acid or methacrylic acids or their derivatives, such as ethylene-acrylic acid, ethylene-methacrylic acid and ethylene-ethyl acrylate copolymers.

6. Styrenic polymers, such as polystyrene (PS) and poly(p-methylstyrene).

7. Styrenic copolymers and terpolymers, such as styrene-butadiene (SBR), styrene-allyl alcohol and styrene-acrylonitrile (SAN), styrene-acrylonitrile-methacrylate terpolymer, styrene-butadiene-styrene block copolymers (SBS), rubber modified styrenics such as styrene-acrylonitrile copolymers modified with acrylic ester polymer (ASA), graft copolymers of styrene on rubbers, such as polybutadiene (HIPS), polyisoprene or styrene-butadiene-styrene block copolymers, graft copolymers of styrene-acrylonitrile on rubbers, such as butadiene (ABS), polyisoprene or styrene-butadiene-styrene block copolymers, graft copolymers of styrene-methyl methacrylate on rubbers, such as polybutadiene (MBS), butadiene-styrene radial block copolymers (e.g. KRO 3 ™ of Phillips Petroleum Co.), selectively hydrogenated butadiene-styrene block copolymers (e.g. Kraton G ™ from Shell Chemical Co.), and mixtures thereof.

8. Polymers and copolymers derived from halogen-containing vinyl monomers, such as poly(vinyl chloride), poly(vinyl fluoride), poly(vinylidene chloride), poly(vinylidene fluoride), poly(tetrafluoroethylene) (PTFE), vinyl chloride-vinyl acetate copolymers, vinylidene chloride-vinyl acetate copolymers and ethylenetetrafluoroethylene copolymers.

9. Halogenated rubbers, such as chlorinated and/or brominated butyl rubbers, such as chlorinated and fluoroelastomers.

10. Polymers and copolymers derived from alpha, beta-unsaturated acids, anhydrides, ester, amides and nitriles or combinations thereof, such as polymers or copolymers of acrylic and methacrylic acids, alkyl and/or glycidyl acrylates and methacrylates, acrylamide and methacrylamide, acrylonitrile, maleic anhydride, maleimide, the various anhydride containing polymers and copolymers described in this disclosure, copolymers of the polymers set forth in this paragraph and various blends and mixtures thereof, as well as rubber modified versions of the polymers and copolymers set forth in this paragraph.

11. Polymers and copolymers derived from unsaturated alcohols or their acylated derivatives, such as poly(vinyl alcohol), poly(vinyl acetate), poly(vinyl stearate), poly(vinyl benzoate), poly(vinyl maleate), poly(vinyl butyral), poly(allyl phthalate), poly(allyl diethylene glycol carbonate) (ADC), ethylene-vinyl acetate copolymer and ethylene-vinyl alcohol copolymers.

12. Polymers and copolymers derived from unsaturated amines, such as poly(allyl melamine).

13. Polymers and copolymers derived from epoxides, such as polyethylene oxide, polypropylene oxide and copolymers thereof, as well as polymers derived from bis-glycidyl ethers.

14. Poly(phenylene oxides), poly(phenylene ethers) and modifications thereof containing grafted polystyrene or rubbers, as well as their various blends with polystyrene, rubber modified polystyrenes or nylon.

15. Polycarbonates and especially the aromatic polycarbonates, such as those derived from phosgene and bisphenols such as bisphenol-A, tetrabromobisphenol-A and tetramethylbisphenol-A.

16. Polyester derived from dicarboxylic acids and diols and/or hydroxycarboxylic acids or their corresponding lactones, such as polyalkylene phthalates (e.g. polyethylene terephthalate (PET), polybutylene terephthalate (PBT) and poly(1,4-dimethylcyclohexane terephthalate) or copolymers thereof) and polylactones, such as polycaprolactone.

17. Polyarylates derived from bisphenols (e.g. bisphenol-A) and various aromatic acids, such as isophthalic and terephthalic acids or mixtures thereof.

18. Aromatic copolyestercarbonates having carbonate, as well as ester linkages present in the backbone of the polymers, such as those derived from bisphenols, iso- and terephthaloyl chlorides and phosgene.

19. Polyurethanes and polyureas.

20. Polyacetals, such as polyoxymethylenes and polyoxymethylenes which contain ethylene oxide as a comonomer.

21. Polysulfones, polyethersulfones and polyimidesulfones.

22. Polyamides and copolyamides which are derived from diamines and dicarboxylic acids and/or from aminocarboxylic acids or the corresponding lactones, such as the following nylons: 6, 6/6, 6/10, 11 and 12.

23. Polyimides, polyetherimides, polyamideimides and copolyetheresters.

24. Crosslinked polymers which are derived from aldehydes on the one hand and from phenols, ureas and melamine on the other hand, such as phenol-formaldehyde, urea-formaldehyde and melamine-formaldehyde resins.

25. Alkyl resins, such as glycerol-phthalic acid resins and mixtures thereof with melamine-formaldehyde resins.

26. Unsaturated polyester resins which are derived from copolyesters of saturated and unsaturated dicarboxylic acids with polyhydric alcohols, as well as from vinyl compounds (crosslinking agents) and also halogen-containing, flame resistant modifications thereof.

27. Natural polymers, such as cellulose, natural rubber, as well as the chemically modified homologous derivatives thereof, such as cellulose acetates, cellulose propionate, cellulose butyrate and the cellulose ethers, such as methyl and ethyl cellulose.

In addition, the stabilizers of this invention may be used to stabilize various combinations or blends of the above polymers or copolymers. They are particularly useful in the stabilization of polyolefins, acrylic coatings, styrenics, rubber modified styrenics, poly(phenylene oxides) and their various blends with styrenics, rubber-modified styrenics or nylon.

The hindered amine light stabilizers of this invention can be used together with other additives to further enhance the properties of the finished polymer. Examples of other additives that can be used in conjunction with the stabilizers of this invention include other antioxidants, such as alkylated monophenols, alkylated hydroquinones, hydroxylated thiodiphenyl ethers, alkylidene-bis-phenols, hindered phenolic benzyl compounds, acylamino-phenols, esters of 3-(3,5-di-t-butyl-4-hydroxyphenyl)propionic acid, esters of 3-(5-t-butyl-4-hydroxy-3-methylphenyl)propionic acid, 3-(3,5-di-t-butyl-4-hydroxyphenyl)propionic acid amides; other UV absorbers and light stabilizers, such as 2-(2'-hydroxyphenyl)-2H-benzotriazoles, 2-hydroxybenzophenones, benzylidene malonate esters, esters of substituted or unsubstituted benzoic acids, diphenyl acrylates, nickel chelates, oxalic acid diamides, other hindered amine light stabilizers; other additives such as metal deactivators, phosphites and phosphonites, peroxide decomposers, fillers and reinforcing agents, plasticizers, lubricants, corrosion and rust inhibitors, emulsifiers, mold release agents, carbon black, pigments, fluorescent brighteners, both organic and inorganic flame retardants and non-dripping agents, melt flow improvers and antistatic agents. Numerous examples of suitable additives of the above type are given in Canadian Patent 1,190,038.

The polymeric derivatives are particularly attractive, offering enhanced compatibility and non-fugitivity when used tostabilize polymer compositions in which they are incorporated.

Preparative Methods

The preparation of the compounds of this invention involves the formation of an imide by reaction of trimellitic acid derivatives and an amino-substituted hindered amine light stabilizer of formula

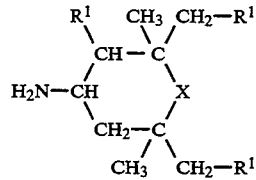

in which $R^1$ and X are as previously defined. Syntheses of such hindered amine light stabilizers are well-known in the art.

Trimellitic acid derivatives which can be used have a general formula

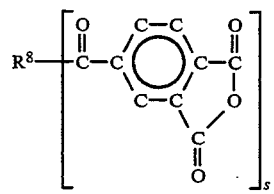

-continued
or

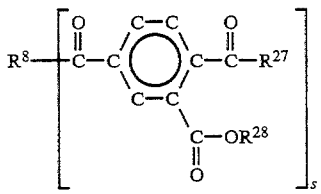

where $R^8$ and s are as previously defined and $R^{27}$ and $R^{28}$ are independently lower alkyl of 1-8 carbons, phenyl or benzyl. The imide formed is formula I.

All the compounds of this invention may be considered as derivatives of the following general formula II which is shown without optional substitution to illustrate the addition product (imide) from two compounds: trimellitic anhydride and 2,2,6,6-tetrasubstituted-4-aminopiperidine derivative shown above:

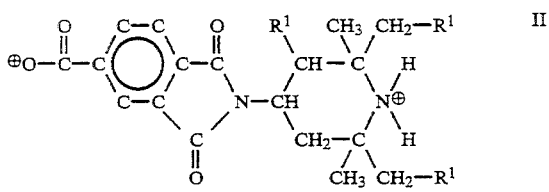

This compound, which contains both carboxylic acid and amine base, exists as an inner salt (iminio carboxylate). This is not necessarily true for all possible derivatives and in more general form the addition product becomes

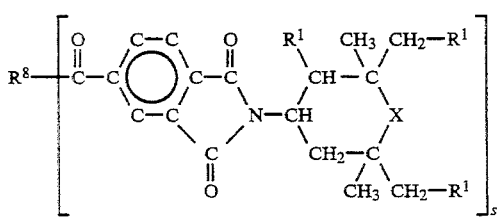

wherein $R^1$, $R^8$, s and X are previously defined.

Depending on the definition of $R^8$, $R^2$ and $R^3$, additional reaction may be necessary to prepare other compounds of this invention. In this case, additional starting materials can be used.

Other starting materials are commercially available amines, alcohols, mercaptans, alkyl halides, amides, anhydrides, acyl halides, chloroformates, epoxides, isocyanates and esters.

Some of the starting materials which can be used in the preparation of this invention are commercially available polymeric materials such as:

1. K-FLEX ® polyester polyols, available from King Industries Specialty Chemicals.

2. FOMREZ ® 53, a hydroxy terminated saturated polyester available from Whitco Chemical Organics Division.

3. JEFFAMINE ® polyoxyalkyleneamines, primary amine terminated polyethers available as monoamines, diamines and triamines, available from Texaco Chemical Company.

4. POLY BD ®, liquid, hydroxy terminated polymers of butadiene, available from ARCO Chemical Company.

5. PERMAPOL ®, polythioether diols available from Products Research & Chemical Corporation.

6. POLYWAX ® OH alcohols, primary linear polymeric alcohols with a fully saturated hydrocarbon backbone, available from Petrolite Corporation.

7. HYCAR ® reactive liquid polymers, hydroxy terminated butadiene/acrylonitrile copolymers available from Goodrich Chemical Company, Chemical Group.

8. RJ-100 ® and RJ-101 ®, styrene/allyl alcohol copolymers available from Monsanto Company.

9. Saytech Experimental Polyol 42-77, a brominated polyester polyol available from Saytech Inc.

10. MAZER ® SFR Reactive Silicone fluids, which are reactive polydimethylsiloxanes with terminal hydroxy sites, available from MAZER Chemicals, Inc.

11. TONE ® Polyols, diols and triols based on polycaprolactone, available from Union Carbide Corporation.

12. DURACARB ® hydroxy terminated aliphatic polycarbonates, available from PPG Industries.

13. Epoxy resins, such as those derived from Bisphenol-A and epichlorohydrin which have 1 or more residual epoxy groups attached to the polymer.

14. NIAX ® polyether polyols available from Union Carbide Corporation.

15. CARBOWAX ® polyethylene glycols and methoxy polyethylene glycols available from Union Carbide Corporation.

16. Any of a number of surfactants with a free hydroxy group, such as TRITON ® X-100, a product of Rohm & Haas company.

In addition, there are many other polymeric derivatives that can be made. The HALS moiety can be attached to any polymer with reactive functionality similar to those discussed above. Particularly useful are polymers containing residues of monomers such as vinyl alcohol, 2-hydroxyethyl (meth) acrylate, glycidyl (meth)acrylate, hydroxypropyl (meth)acrylate. Additional commercially available polymers have hydroxy groups along the polymer chain or as end groups. Examples of these types of polymers are Bisphenol-A polycarbonate, polyphenylene oxide, hydroxypropyl cellulose and hydroxypropyl methyl cellulose.

Inner salt II is a versatile intermediate for further elaboration into additional compositions of this invention. In addition to the preparation methods set forth in detail in the examples, another method of preparing inner salt II would involve the reaction of the amino-substituted piperidine with an appropriate diester, esteracid, amide-ester, ester-acid chloride or diacid dichloride. Such preparations are described in the chemical literature.

Esterification of inner salt II may be accomplished in many ways. Alkylation by a reactive alkyl chloride, bromide or iodide can be done under neutral or alkaline conditions in a solvent, such as aromatic hydrocarbons, chlorinated alkanes, ketones (such as acetone, methyl ethyl ketone), ethers (such as methyl t-butyl ether, tetrahydrofuran), amides (such as N-methylpyrrolidone, N,N-dialkylformamide), sulfolane or dimethylsulfoxide, alone or in combination. Esterification by epoxides is carried out in a similar manner. The concentration of reactants in the solvent is not critical as long as both reactants are at least partially soluble. The preferred solvent is dimethylformamide or solvent mixtures in which it is present. The mole ratio of inner salt II to alkylating agent can range from about 1:1 to about 1:10 and varies based on the desired product. If the hindered amine is not tertiary (X=—NH— or —NH$_2^{\oplus}$—) before this reaction, the alkylation may include both carboxyl and amine substitution. This can be controlled via stoichiometry to favor only alkylation of carboxyl (1 equivalent alkylating agent) to alkylation of both carboxyl and amine (two equivalents or more). The alkylation can be done in the presence of an acid acceptor, such as a tertiary amine, or an inorganic base, such as an alkali metal carbonate, bicarbonate or hydroxide. The added base is required to liberate the amine if it is participating in a salt. Time and temperature conditions are such that the reaction proceeds at a reasonable rate. Typical conditions would be ambient temperature up to the refluxing temperature of the chosen solvent (up to about 200° C.) and a reaction duration of about 1 to about 72 hours. The preferred temperature range is room temperature up to about 150° C.

Also beneficial in certain instances is the inclusion of a phase transfer catalyst (PTC) to enable the reaction either by increasing its rate or by aiding dissolution of the starting materials. The amount of PTC is generally about 0.01 to about 0.5 mole % based on inner salt II, preferably about 0.05 to about 0.2 mole %. An example of a PTC would be a tetraalkylammonium halide. Many such compounds are commercially available.

The acid halide of inner salt II is a versatile intermediate which is prepared by contacting the free acid or an alkali metal salt with a reactive halogenating agent, such as thionyl chloride, thionyl bromide, phosphorus trichloride or tribromide, phosphorus pentachloride, phosphorous pentabromide, phosphorus oxychloride or other known halogenating agents. This reaction is best done using excess halogenating agent as solvent, although inert solvents, such as aromatic hydrocarbons or halogenated alkanes may also be used. The formation reaction can be done at a variety of temperatures for various time periods depending upon the reactivity of the halogenating agent and the acid derivative. Temperatures from ambient up to refluxing solvent (up to about 150° C.) may be employed. The reaction is continued until conversion is complete, generally about 1 to about 24 hours or longer.

The product of reaction is the ammonium salt of the acid halide and this often precipitates from the reaction mixture as formed. In this instance, the product is conveniently isolated by filtration from the reaction mixture. If the product does not precipitate, the solvent and excess halogenating agent is stripped away from the product using common methods. This intermediate must be protected from moisture which hydrolyzes it back to the acid. A preferred method is described in the examples section.

The monoester or polyester, thioester and amide derivatives (or mixtures thereof) can be prepared via the acid halide intermediate, by reaction with the appropriate monoalcohol or polyalcohol, amine or mercaptan (or mixture). This acylation reaction is best carried out in solvent with an acid acceptor to remove the halogen acid as formed and to free the acid halide ammonium salt. An excess of the compound being acylated is desirable, especially for monoacylated compositions. In the case of the monoamine or polyamine starting materials, excess amine can serve as the halogen acceptor. In the case of the monoalcohol or polyalcohol or mercaptan starting materials, an additional base, either a tertiary amine or an inorganic base, such as an alkali metal carbonate, bicarbonate or hydroxide, can be used. The mole ratio of alcohol, mercaptan and amine groups to the acid halide is calculated based on the equivalents of reactive hydroxy, mercapto and amino groups available and the desired degree of substitution, providing one equivalent of acid halide for each equivalent of hydroxy, mercaptan or amine to be acylated. For a heterogeneous base, a PTC as described above can be beneficial. The acylation reaction may be carried out over a wide range of temperatures, particularly ambient temperature up to the refluxing temperature of the reaction medium (up to about 200° C.). The duration of the reaction is chosen based on product and the rate of conversion of starting material to product and can vary from about 1 to about 72 hours.

The hydrazide (General Formula I where $R^8$ is NHNH$_2$) may be prepared by reacting the esters (where $R^8$ is $R^{11}$—O—), halides (where $R^8$ is chloro or bromo) and amides (where $R^8$ is —N($R^{11}$)($R^{12}$) with hydrazine or hydrazine hydrate. Typically, the ester used is dissolved in a polar solvent and converted to the desired hydrazide by stirring with an equivalent amount or slight excess of hydrazine or hydrazine hydrate. The reaction may go at room temperature or may require heating. Preferably the hydrazinolysis reaction is carried out on a lower alkyl ester in methanol or ethanol. Substituted hydrazides can be prepared by reacting the esters with substituted hydrazines.

Other derivatives of the parent hydrazide are hydrazones, carbamoyl and thiocarbamoyl derivatives which may be prepared by reacting the hydrazides with ketones, aldehydes, isocyanates, disocyanates, isothiocyanates or diisothiocyanates. Such reactions are well known in the art and can occur under a wide variety of temperatures, times, solvents and concentrations. Generally, a mole ratio of about 0.9 to about 1.0 to about 1.1 to about 1.0 of the hydrazide to the monofunctional coreactant is employed. If the coreactant is difunctional, then a mole ration of about 1.8 to about 2.0 to about 1.1 to about 1.0 of the hydrazide to the difunctional coreactant is employed. If the coreactant is a compound that can easily be removed from the product, e.g. acetone or methyl ethyl ketone, lower mole ratios may be desirable. In fact, it may be desirable to use the coreactant as the solvent.

The acyl derivatives of the hydrazide may be prepared by reacting the ester (as described above) with acid hydrazides in refluxing alcohol (i.e., methanol).

The alkoxycarbonyl, cycloalkoxycarbonyl, aryloxycarbonyl and aralkoxycarbonyl derivatives of the hydrazide may be prepared by reacting the ester (as described above) with the corresponding alkyl, cycloalkyl, aryl or aralkyl carbazates in refluxing alcohol (i.e., methanol). Alternately, these derivatives may be prepared by reacting the hydrazide with a disubstituted carbonate or substituted haloformate. When a haloformate is used, an additional base (inorganic or amine) may be used to react with the halogen acid formed.

The alkyl derivatives of the hydrazide may also be prepared by reacting the hydrazides with epoxides. The reactions are generally carried out neat or in a minimum amount of a high boiling solvent. Reaction generally occurs quite readily at about 140° C. to about 150° C. The hydrazide group reacts with two equivalents of epoxide. The ratio of the unsubstituted hydrazide to the monoalkylated and dialkylated products is dependent upon the mole ratio of epoxide to hydrazide, the temperature and the concentration if the reaction is run in a solvent.

Polymeric derivatives can be prepared by five main methods: acylation of polymers bearing reactive hydroxy, amino, mercapto or epoxy groups; (co)polymerization of derivatives of the acid, as for example, 2-(methacryloyloxy)ethyl ester or the allyl ester; graft polymerization of the same monomeric HALS onto a polymer backbone; functionalization of condensation polymers through use of a molecular weight regulator; and attachment of a suitably structured HALS derivative through its use as a chain transfer agent.

The acylation is conducted as described previously.

The polymerization of monomeric derivatives either alone or with other monomers is performed using any of the well known methods employed in the art for copolymerizing ethylenic or vinyl aromatic monomers with the monomer functionality incorporated into the HALS-imide. Description of such methods are described in *Kirk-Othmer Encyclopedia of Chemical Technology*, 3rd Ed , Vol 18, "Polymerization Mechanisms and Processes", pp. 720–744. In addition, 5 to 40 percent by weight of one of the known elastomers may be incorporated into the copolymer by copolymerizing the monomers in the presence of the rubber. Preferably, the elastomers are incorporated into the monomer mixture prior to polymerization using, for example, the methods of U.S. Pat. Nos. 4,097,551 or 4,486,570. Preferred rubbers are diene rubbers, such as homopolymers of conjugated dienes, such as butadiene, isoprene, chloroprene or piperylene and copolymers of such dienes with up to 50 mole percent of one or more copolymerizable monoethyleneically unsaturated monomers, such as styrene, substituted styrenes, acrylonitrile, methacrylonitrile or isobutylene.

The polymeric derivatives can also be prepared by grafting the monomeric HALS-imide onto a polymer. The polymer may be high or low density polyethylene, a polypropylene or a copolymer of alpha olefins having up to about six carbons, or any other polymer having a labile hydrogen on the polymer backbone. Examples of such copolymers are ethylene-butene-1, ethylene-propylene and propylene-butene-1 copolymers. The method of grafting the HALS monomer onto the polymers is similar to the methods known in the art for such reactions. Briefly, the preparation comprises treating the polymer with a free radical initiator which generates free radicals on the polymer. The free radical sites on the polymer can then add on the unsaturated HALS-monomer. Active radical sites on the polymer backbone can also be induced by subjecting the polymer to the action of high energy ionizing radiation, such as gamma rays, X-rays or high speed electrons or by simply milling the polymer in the presence of air. Examples of applicable methods are described in U.S. Pat. Nos. 3,483,276 and 4,506,056.

The free acid group in the HALS derivative can be used to control the molecular weight of polymers prepared by condensation polymerization, such as polyamides, polycarbonates and polyesters. The technique of adding a monobasic acid for molecular weight control is well known in the art. In this process, the monobasic acid (in this case the HALS derivative) becomes attached to the polymer molecule as an endgroup.

A HALS derivative with a labile hydrogen can be introduced into a polymerization mixture as a chain transfer agent. In this capacity, the HALS would also be incorporated as a polymer end group. The mechanism here comprises termination of a growing polymer chain by donation of the labile hydrogen and initiation of another polymer chain from the active site thus formed on the HALS molecule. Such a technique is known in the art.

The invention will now be described in more detail with reference to the following specific, non-limiting examples. In the following examples where appropriate, analytical data is included to further define the products. All melting points are uncorrected. Spectral data was obtained using common practices. All NMR spectra were recorded in chloroform-d (unless otherwise specified) relative to tetramethylsilane (0.0 ppm).

EXAMPLE 1

Preparation of N-(2,2,6,6-tetramethyl-4-piperidinyl)-4-carboxyphthalimide, internal salt Into a 2 liter round bottom flask equipped with a mechanical stirrer, nitrogen atmosphere and thermometer were placed 149.5 g (0.75 mol) trimellitic anhydride and 500 ml of acetic acid. This mixture was cooled and stirred while 34.1 g (0.85 mol) sodium hydroxide (solid) were added (exothermic). After addition of base, cooling was discontinued and the mixture was stirred while 128.9 g (0.82 mol) of 4-amino-2,2,6,6-tetramethylpiperidine were slowly added, using an additional 250 ml of acetic acid to rinse the amine into the flask. This addition was also exothermic and the heat evolved was used to warm the reaction mixture to about 90° C. After complete addition, the reaction was refluxed for 2 hours. The hot reaction mixture was poured onto 1000 g ice in a beaker and the mixture stirred until the ice melted. The solid product was isolated by filtration and slurried twice with 700 ml portions of acetone. A significant static charge complicates handling of the product. The white product weighed 216.2 g (87.3% theoretical). The infrared spectrum (KBr pellet) of this compound showed the carbonyl absorptions for the imide (1700 $cm^{-1}$) and the carboxylate (1620 $cm^{-1}$). The piperidinium salt N-H was indicated by a broad band 2000–3000 $cm^{-1}$. During heating at 20° C./minute in the differential scanning calorimeter, the salt began decomposing at about 350° C.

EXAMPLE 2

Preparation of N-(2,2,6,6-tetramethyl-4-piperidinyl)-4-(chlorocarbonyl)phthalimide, hydrochloride salt Into a dry 500 ml round bottom flask equipped with a magnetic stirrer, reflux condenser and nitrogen atmosphere were placed 175 g (1.5 mol) thionyl chloride. 69.9 g (0.21 mol) N-(2,2,6,6-tetramethyl-4-piperidinyl)-4-carboxyphthalimide were added in small portions over a 45 minute period. The resulting mixture was refluxed for an hour before stirring became difficult (due to precipitated product) and 25 g (0.21 mol) thionyl chloride was added to alleviate this problem. The mixture was refluxed for three additional hours. The reaction mixture was cooled to room temperature and diluted with 600 ml methyl t-butyl ether. The solid product was isolated by filtration and washed on the funnel with three 100 ml portions of ether. Final removal of solvent was accomplished under high vacuum, giving 76.7 g white crystals. By analysis for hydrolyzable chloride, the sample was determined to be 99+% assay. The yield was 94.8%. The infrared spectrum (KBr pellet) of this compound showed the carbonyl absorptions for the imide (1705 cm$^{-1}$) and the carbonyl chloride (1750 cm$^{-1}$).

EXAMPLE 3

Preparation of
N-(2,2,6,6-tetramethyl-4-piperidinyl)-4-(aminocarbonyl)phthalimide Into a 125 ml Erlenmeyer flask equipped with a thermometer were placed 50 ml concentrated aqueous ammonium hydroxide. The acid chloride of Example 2 (5.0 g, 0.013 mol) was added and the mixture stirred for 30 minutes. The solid product was collected by filtration and washed with several portions of water. The product was dried briefly on the funnel, then dissolved in hot methanol and filtered (hot). Upon cooling the product crystallized. The crystallized material was isolated by filtration, yielding 1.1 g of white crystals (melting at 189°–194° C.). Reduction of the crystallization solvent produced a second crop of product, 0.25 g (melting at 189°–200° C.). The infrared spectrum (KBr pellet) of the product showed an intense broad carbonyl for both the amide and the imide at 1680–1720 cm$^{-1}$.

EXAMPLE 4

Preparation of
N-(2,2,6,6-tetramethyl-4-piperidinyl)-4-(ethoxycarbonyl)phthalimide Into a 125 ml reaction flask equipped with magnetic stirrer, thermometer, addition funnel and nitrogen atmosphere were placed 5.0 g (0.013 mol) of acid chloride from Example 2 and 25 ml ethanol. The addition funnel was charged with 15 ml ethanol and 2.8 g (0.028 mol) triethylamine. The reaction mixture was stirred as the base was added over a 5 minute period accompanied by a 10° C. exotherm. The mixture was stirred at ambient temperature for 2 hours, during which time suspended solid slowly dissolved. The reaction mixture was stripped of solvent using an aspirator vacuum. The solid was taken up in 100 ml toluene in a separatory funnel and washed with 50 ml saturated sodium bicarbonate and three 50 ml portions of water. The toluene solution was dried with anhydrous magnesium sulfate and stripped of solvent to yield 4.0 g of product. This material was recrystallized from 95% ethanol, producing 2.6 g of white crystals (melting at 115°–121° C.). The infrared spectrum (KBr pellet) of the product showed a doublet carbonyl with absorbance maxima of 1705 cm$^{-1}$ (imide) and 1710 cm$^{-1}$ (ester). The NMR spectrum indicated the presence of the ethyl group (4.4 ppm, quartet, 2H; 1.4 ppm, triplet) and the aromatic ring (7.8–8.0 ppm, doublet, 1H; 8.3–8.5, multiplet, 2H) and the HALS group [4.5–4.8 ppm, multiplet, 1H; 1.0–2.3 ppm several multiplets including two singlets (1.2 and 1.3 ppm)].

EXAMPLE 5

Preparation of
N-(2,2,6,6-tetramethyl-4-piperidinyl)-4-(2,2,6,6-tetramethyl-4-piperidinyloxycarbonyl)phthalimide Into a 125 ml reaction flask equipped with a magnetic stirrer, thermometer, condenser and nitrogen atmosphere were placed 5.0 g (0.013 mol) of the acid chloride of Example 2 and 50 ml of 2% dimethylformamide in methylene chloride. This mixture was stirred during the addition of 2.1 g (0.013 mol) 2,2,6,6-tetramethyl-4-piperidinol and 2.8 g (0.028 mol) triethylamine. The reaction was then refluxed for 3 hours. The mixture was cooled and transferred to a separatory funnel with 100 ml methylene chloride, 25 ml water and 50 ml 5% sodium hydroxide. The mixture was shaken, allowed to separate and the organic phase drawn off. The aqueous phase (and interfacial solid) was extracted with an additional 25 ml solvent. The combined organic solutions were dried with anhydrous magnesium sulfate and the solvent stripped using aspirator vacuum. The product was 4.1 g of slightly yellow crystals (melting at 196°–200° C.). The infrared spectrum (chloroform) showed the carbonyl absorption at 1705 cm$^{-1}$ (imide and ester). The NMR Spectrum showed the anticipated aromatic ring (7.7–7.9 ppm, doublet, 1H; 8.3–8.5, multiplet, 2H) and two HALS groups [5.2–5.7 ppm, multiplet, 1H; 4.4–4.9 ppm, multiplet, 1H; 1.0–2.3 ppm, several multiplets including two singlets (1.2 and 1.3 ppm)]. The UV spectrum showed an absorbance maximum (THF) at 296 nm, molar absorptivity 300.

EXAMPLE 6

Preparation of
N-(2,2,6,6-tetramethyl-4-piperidinyl)-4-[(2-ethylhexyloxy)carbonyl]phthalimide Into a 125 ml reaction flask equipped with a magnetic stirrer, thermometer, condenser and nitrogen atmosphere were placed 5.0 g (0.013 mol) of the acid chloride of Example 2, 1.7 g (0.013 mol) 2-ethylhexanol and 50 ml of 2% dimethylformamide in methylene chloride. This mixture was stirred during the addition of 2.8 g (0.028 mol) triethylamine in 5 ml methylene chloride. This addition produced an exotherm of about 10° C. The reaction was then refluxed for 1 hour. The mixture was cooled and transferred to a separatory funnel with 100 ml methylene chloride and 250 ml water. The ensuing emulsion was filtered, put back in the funnel and the phases separated. The organic phase was extracted with 50 ml water and 50 ml 5% sodium bicarbonate. The organic solution was dried with anhydrous magnesium sulfate and the solvent stripped using aspirator and high vacuum. Liquid chromatographic analysis of the white solid product indicated the presence of two components. The material was redissolved in methylene chloride and extracted with two 50 ml portions of 5% sodium hydroxide. The organic solution was again dried and stripped and the residue recrystallized from 80/20 ethanol/water. After isolation and drying, 1.5 g of slightly yellow product were obtained (melting 129°–131° C.). The infrared spectrum (KBr pellet) showed the carbonyl absorption at 1720 cm$^{-1}$ (imide and ester). The NMR spectrum showed the anticipated aromatic ring (7.7–7.9 ppm, doublet, 1H; 8.2–8.5, multiplet, 2H) and the 2-ethylhexyl and HALS groups [4.4–4.9 ppm, multiplet, 1H; 4.2–4.3 ppm, doublet, 1H; 0.7–2.3 ppm, several multiplets including two singlets (1.2 and 1.3 ppm )].

EXAMPLE 7

Preparation of
N-(2,2,6,6-tetramethyl-4-piperidinyl)-4-(dodecylaminocarbonyl)phthalimide Into a 125 ml reaction flask equipped with a magnetic stirrer, thermometer, condenser and nitrogen atmosphere were placed 2.4 g (0.013 mol) dodecylamine and 40 ml of 2% dimethylformamide in methylene chloride. This mixture was stirred during the addition of 5.0 g (0.013 mol) of the acid chloride of Example 2 accompanied by an 8° C. exotherm. The reaction mixture was cooled to ambient temperature and 2.8 g (0.028 mol) triethylamine was added, producing an exotherm of about 10° C. The reaction was allowed to stir at room temperature for 30 minutes then transferred to a separatory funnel with 50 ml methylene chloride and 50 ml water. The phases were separated and the organic phase was further extracted with three 50 ml portions of water. Additional solvent, 50 ml, was added and the organic solution washed with two 50 ml portions of 5% sodium hydroxide. The organic solution was dried with anhydrous magnesium sulfate and the solvent stripped using aspirator and high vacuum systems. The product was 6.1 g (98% of theory) of a yellow semi-solid which upon standing became a solid (melting at 42°–45° C.). The infrared spectrum (chloroform) showed two carbonyl absorptions at 1720 cm$^{-1}$ (imide) and 1660 cm$^{-1}$ (amide). The NMR spectrum showed the anticipated aromatic ring (7.7–7.9 ppm, doublet, 1H; 8.1–8.3, multiplet, 2H), the amide N-H (6.4–6.8 ppm, multiplet, 1H), the amide methylene (3.2–3.7 ppm, multiplet, 2H) and HALS group and amide residue [4.4–4.9 ppm, multiplet, 1H; 0.7–2.3 ppm, several multiplets].

EXAMPLE 8

Preparation of N-(2,2,6,6-tetramethyl-4-piperidinyl)-4-(dibutylaminocarbonyl)phthalimide Into a 125 ml reaction flask equipped with a magnetic stirrer, thermometer, condenser and nitrogen atmosphere were placed 5.0 g (0.013 mol) of acid chloride of Example 2 and 50 ml of 2% dimethylformamide in methylene chloride. This mixture was stirred during the addition of 1.7 g (0.013 mol) of di-n-butylamine accompanied by a 10° C. exotherm. The reaction mixture was cooled to ambient temperature and 2.8 g (0.028 mol) triethylamine were added, producing an exotherm of about 10° C. The reaction was cooled to room temperature and allowed to stir for 1 hour, then transferred to a separatory funnel with 50 ml methylene chloride and 50 ml water. Upon shaking, an emulsion formed which was broken by the addition of 25 ml of 5% sodium hydroxide. The phases were separated and the organic phase was further extracted with three 50 ml portions of 5% sodium hydroxide and three 50 ml portions of water. The organic solution was dried with anhydrous magnesium sulfate and the solvent stripped using aspirator and high vacuum systems. The product was 5.0 g of a yellow liquid. The infrared spectrum (between salt plates) showed two carbonyl absorptions at 1718 cm$^{-1}$ (imide) and 1642 cm$^{-1}$ (amide). The NMR spectrum showed the anticipated aromatic ring (7.5–8.0 ppm, multiplet, 3H), the amide methylene hydrogens (2.9–3.8 ppm, broad doublet, 4H) and the HALS group [4.4–4.9 ppm, multiplet, 1H; 0.5–2.3 ppm, several multiplets including two singlets (1.2 and 1.3 ppm)].

EXAMPLE 9

Preparation of N-(2,2,6,6-tetramethyl-4-piperidinyl)-4-(2,2,6,6-tetramethyl-4-piperidinylaminocarbonyl)phthalimide A. From the Acid Chloride of Example 2:

Into a 125 ml reaction flask equipped with a magnetic stirrer, thermometer, condenser and nitrogen atmosphere were placed 2.1 g (0.013 mol) of 2,2,6,6-tetramethyl-4-amino-piperidine and 50 ml of 2% dimethylformamide in methylene chloride. To this was added triethylamine (2.8 g, 0.028 mol). This mixture was stirred and cooled during the addition of 5.0 g (0.013 mol) of acid chloride of Example 2, accompanied by an exotherm to 40° C. The reaction was allowed to stir at room temperature for 1 hour. The mixture was transferred to a separatory funnel with 100 ml methylene chloride, 150 ml water and 50 ml of 5% sodium hydroxide. The phases were separated and the aqueous phase extracted with an additional 50 ml of methylene chloride. The organic solutions were combined and washed with three 100 ml portions of water. The organic solution was dried with anhydrous magnesium sulfate and the solvent stripped using aspirator and high vacuum systems. The product was 1.1 g of a white solids. This solid was recrystallized from toluene to give 0.8 g of white crystals, melting at 260°–262° C. The infrared spectrum (chloroform) showed the carbonyl absorption at 1710 cm$^{-1}$ (imide) and 1665 cm$^{-1}$ (amide). The NMR spectrum showed the anticipated aromatic ring (7.7–7.9 ppm, doublet, 1H; 8.0–8.3, multiplet, 2H), the amide N-H (5.9–6.1 ppm, doublet, 1H) and the HALS groups [4.2–4.9 ppm, multiplet, 2H; 0.8–2.3 ppm, several multiplets including two singlets (1.2 and 1.3 ppm)].

B. From trimethyl 1,2,4-benzenetricarboxylate:

Into a 100 ml flask equipped with reflux condenser and oil bath were combined 2,2,6,6-tetramethyl-4-aminopiperidine (2.7 g, 0.017 mol), trimethyl 1,2,4-benzenetricarboxylate (2.0 g, 0.008 mol), potassium t-butoxide (0.04 g) and 50 ml of mesitylene. This mixture was refluxed 28 hours, cooled and transferred to a separatory funnel with 100 ml methylene chloride. The organic solution was washed with three 50 ml portions of water and dried with anhydrous magnesium sulfate. The solvent was stripped using aspirator and high vacuum systems. The residue was mixed with 50 ml pentane and set aside for crystallization of the product. The crystallized product was isolated by filtration, yielding 0.6 g of white crystals. This product was recrystallized from toluene, producing 0.1 g of white crystals with a melting point and infrared spectrum in agreement with that obtained for the product from procedure A in this example.

EXAMPLE 10

Preparation of styrene/allyl alcohol/N-(2,2,6,6-tetramethyl-4-piperidinyl)-4-allyloxycarbonylphthalimide copolymer Into a 125 ml reaction flask equipped with a magnetic stirrer, thermometer, condenser and nitrogen atmosphere were placed 5.0 g (0.013 mol) of acid chloride of Example 2 and 50 ml of 2% dimethylformamide in methylene chloride. This mixture was stirred during the addition of 2.9 g (about 0.013 hydroxy equivalents) of RJ ® 101 (a styrene/allyl alcohol copolymer from Monsanto having 7.7±0.3 wt % hydroxy content). 2.8 g (0.028 mol) triethylamine were added. The reaction was refluxed for 1.5 hours. The mixture was transferred to a separatory funnel with 150 ml methylene chloride and 100 ml of 5% sodium hydroxide. The phases were separated and the organic phase was further extracted with three 50 ml portions of 5% sodium hydroxide and 50 ml water. The organic solution was dried with anhydrous magnesium sulfate and the solvent stripped using aspirator and high vacuum systems. The product was 4.3 g of light yellow crystals. The solid was redissolved in a minimum amount of methylene chloride and precipitated by dropwise addition to 800 ml of hexane. The solid was isolated by filtration yielding 3.9 g. The infrared spectrum (KBr pellet) showed the carbonyl absorption at 1715 cm$^{-1}$ (imide and ester). The Tg was determined to be 87.6° C. Molecular weight data obtained from gel permeation chromatography indicated an Mn of 1400 and an Mw of 2100 (based on polystyrene standard). The NMR spectrum demonstrated the presence of the HALS moiety in the high molecular weight material (two singlets at 1.2 and 1.3 ppm) and the presence of aromatic hydrogens from the pendant phenyl groups.

EXAMPLE 11

Preparation of 4,4'-[2,5-dioxa-1,6-dioxohexane-1,6-diyl] bis[N-(2,2,6,6-tetramethyl-4-piperidinyl)phthalimide]

Into a 125 ml reaction flask equipped with a magnetic stirrer, thermometer, condenser and nitrogen atmosphere were placed 6.5 g (0.017 mol) of acid chloride of Example 2 and 50 ml of 2% dimethylformamide in methylene chloride. This mixture was stirred during the addition of 0.43 g (0.007 mol) of ethylene glycol. 7.3 g (0.072 mol) of triethylamine were added, accompanied by an exotherm to 40° C. The reaction was refluxed for 4 hours. Acid chloride (1.0 g, 0.003 mol) was added and the reflux continued for an additional 2 hours. The mixture was cooled and transferred to a separatory funnel with 50 ml methylene chloride and extracted with one 100 ml portion of 5% sodium hydroxide, two 50 ml portions of 5% sodium hydroxide and three 50 ml portions of water. The organic solution was dried with anhydrous magnesium sulfate and the solvent stripped using aspirator and high vacuum systems. The solid residue was recrystallized from 95% ethanol. The recrystallized solid was dissolved in methylene chloride and dried again with anhydrous magnesium sulfate. The solvent was stripped using aspirator and high vacuum systems yielding 2.6 g of yellow solid melting at 70° C. The infrared spectrum (KBr pellet) showed the carbonyl absorption at 1715 cm$^{-1}$ (imide and ester). The NMR spectrum showed the anticipated aromatic ring (7.7–7.9 ppm, doublet, 1H; 8.3–8.5, multiplet, 2H), the HALS N—C—H and the methylenes merged (4.2–5.0 ppm, multiplet with prominent singlet at 4.7 ppm) and the HALS groups [1.1–2.3 ppm, several multiplets including two singlets (1.2 and 1.3 ppm)].

This same product can be prepared from ethylene bis trimellitate (AC-32, a product of Anhydride and Chemical Incorporated), using the procedure described in Example 29. The commercial bis anhydride is a mixture and the product obtained is not as pure as that prepared above.

EXAMPLE 12

Preparation of 4,4'-[1,3-phenylenedi(oxycarbonyl)]-bis[N-(2,2,6,6-tetramethyl-4-piperidinyl]phthalimide Into a 125 ml reaction flask equipped with a magnetic stirrer, thermometer, condenser and nitrogen atmosphere were placed 5.0 g (0.013 mol) of acid chloride of Example 2 and 50 ml of 2% dimethylformamide in methylene chloride. This mixture was stirred during the addition of 1.43 g (0.013 mol) of resorcinol. 2.8 g (0.028 mol) of triethylamine were added, accompanied by a small exotherm, but the temperature was kept between 20 and 25° C. by using an ice bath. The reaction was stirred at room temperature for 2 hours. The mixture was transferred to a separatory funnel with 50 ml water, the phases were allowed to separate and the aqueous solution was washed with 50 ml of fresh methylene chloride. The combined organic solutions were washed with two 50 ml portions of 5% sodium hydroxide. The organic material was then dried with anhydrous magnesium sulfate and the solvent stripped using aspirator and high vacuum systems. The product was 1.8 g of a yellow solid melting at 130°–135° C. The infrared spectrum (KBr pellet) showed two carbonyl absorptions at 1710 and 1745 cm$^{-1}$ (imide and ester). The NMR spectrum showed the anticipated aromatic rings (7.8–8.0 ppm, doublet, 1H; 8.4–8.6, multiplet, 2H; 7.0–7.6 ppm, multiplet with prominent peak at 7.2 ppm), the HALS group [4.4–4.9 ppm, multiplet, 1H; 1.1–2.3 ppm, several multiplets including two singlets (1.2 and 1.3 ppm)]. The UV spectrum showed an absorbance maximum (THF) at 300 nm.

EXAMPLE 13

Preparation of N-(2,2,6,6-tetramethyl-4-piperidinyl)-4-[octylphenoxypoly(ethoxy)carbonyl]phthalimide Into a 125 ml reaction flask equipped with a magnetic stirrer, thermometer, condenser and nitrogen atmosphere were placed 5.0 g (0.013 mol) of acid chloride of Example 2, 50 ml of 2% dimethylformamide in methylene chloride and TRITON X-100 ® (octylphenoxypoly(ethoxy)ethanol, a product of Rohm and Haas Co., 4.6 g). 1.5 g (0.015 mol) triethylamine were added, accompanied by a small exotherm. The reaction cleared, then a solid formed as the mixture was heated to reflux. The reaction was refluxed for 4 hours, then cooled to room temperature and transferred to a separatory funnel with 50 ml methylene chloride and 50 ml of 5% sodium hydroxide. The phases were allowed to separate and the aqueous solution was washed with three 100 ml portions of fresh methylene chloride. The organic material was then dried with anhydrous magnesium sulfate and the solvent stripped using aspirator and high vacuum systems. The product was 6.0 g of a viscous liquid. The infrared spectrum (between salt plates) showed two carbonyl absorptions at 1710 and 1685 cm$^{-1}$ (imide and ester). The NMR spectrum showed the anticipated aromatic rings (7.8–8.0 ppm, doublet; 8.3–8.6, multiplet; 6.7–7.4 ppm, multiplet). The ethylene groups were a prominent singlet at 4.7 (with several smaller peaks at the base) and the HALS and octyl groups were present (0.6–2.3 ppm, several multiplets including a singlet at 0.8 ppm). The integration of this spectrum indicated that the sample contained considerable unreacted starting alcohol. A crude assay based on this integration indicated the title compound was present in about 50%.

EXAMPLE 14

Preparation of N-(2,2,6,6-tetramethyl-4-piperidinyl)-4-(allyloxycarbonyl)phthalimide Into a 125 ml reaction flask equipped with a magnetic stirrer, thermometer, condenser and nitrogen atmosphere were placed 5.0 g (0.013 mol) of acid chloride of Example 2, 50 ml of 2% dimethylformamide in methylene chloride and allyl alcohol (0.7 g, 0.012 mol). Triethylamine (2.8 g, 0.028 mol) was added, accompanied by an exotherm from room temperature up to 35° C. The reaction was cooled to room temperature and stirred for 1.5 hours, then transferred to a separatory funnel with 50 ml methylene chloride and 50 ml of 5% sodium hydroxide. The phases were allowed to separate and the aqueous solution was washed with an additional 50 ml of fresh methylene chloride. The combined organic solutions were then dried with anhydrous magnesium sulfate and the solvent stripped using aspirator and high vacuum systems. The product was 3.8 g of a yellow solid melting at 90°–93° C. The solid was recrystallized in methyl t-butyl ether, producing almost white crystals melting at 96°–98° C. The infrared spectrum (KBr pellet) showed the carbonyl absorption at 1715 cm$^{-1}$ (imide and ester). The NMR spectrum showed the anticipated aromatic ring (7.7–7.9 ppm, doublet, 1H; 8.2–8.5, multiplet, 2H), a typical allyl group pattern merging with the N—C—H of the HALS group (4.8–6.3 ppm for allyl and 4.4–4.9 ppm for HALS, several multiplets, 6H) and the rest of the HALS group [0.8–2.3 ppm, several multiplets including two singlets (1.2 and 1.3 ppm)].

EXAMPLE 15

Reaction of JEFFAMINE ® D-230 with the Acid Chloride of Example 2

Into a 125 ml reaction flask equipped with a magnetic stirrer, thermometer, condenser and nitrogen atmosphere were placed 5.0 g (0.013 mol) of acid chloride of Example 2, 50 ml of 2% dimethylformamide in methylene chloride and JEFFAMINE ® D-230 (an amine terminated polypropylene oxide, product of Texaco Chemical Co., 1.5 g). The amine addition caused a small exotherm. Triethylamine (2.8 g, 0.028 mol) was added, accompanied by an exotherm from room temperature up to 35° C. The reaction was stirred at ambient temperature for 2.5 hours. The mixture was transferred to a separatory funnel with 100 ml methylene chloride and 100 ml of 5% sodium hydroxide. The phases were allowed to separate and the organic was washed with two 50 ml portions of 5% sodium hydroxide and three 50 ml portions of water. The organic solution was then dried with anhydrous magnesium sulfate and the solvent stripped using aspirator and high vacuum systems. The product was 4.8 g of white crystals. The infrared spectrum (KBr pellet) showed two carbonyl absorptions at 1710 and 1650 cm$^{-1}$ (imide and amide). The Tg was determined to be 61.6° C. The NMR spectrum showed the anticipated aromatic ring (7.7–7.9 ppm, doublet; 8.0–8.3, multiplet); and the presence of the HALS group, indicated by two singlets at 1.2 and 1.3 ppm.

EXAMPLE 16

Reaction of the Acid Chloride of Example 2 with Poly(butadiene) diol

Into a 125 ml reaction flask equipped with a magnetic stirrer, thermometer, condenser and nitrogen atmosphere were placed 1.9 g (0.005 mol) of acid chloride of Example 2, 50 ml of 2% dimethylformamide in methylene chloride and polybutadiene diol (nominal M. W. 2800, a product of Scientific Polymer Products, Inc.) (5.0 g). Triethylamine (1.0 g, 0.01 mol) was added, accompanied by a small exotherm. The reaction was stirred at room temperature for 2 hours. The mixture was transferred to a separatory funnel with 100 ml methylene chloride and washed with three 50 ml portions of 5% sodium hydroxide (making the best possible separations of the emulsified mixture). The aqueous washes were combined and further diluted with 100 ml water and extracted with 250 ml methylene chloride. The organic solutions were combined then dried with anhydrous magnesium sulfate and the solvent stripped using aspirator and high vacuum systems. The product was 5.4 g of viscous dark yellow liquid. The infrared spectrum (between salt plates) showed several carbonyl absorptions with a broad major absorption at 1710 cm$^{-1}$. The NMR spectrum demonstrated the presence of the aromatic rings and intense methylene absorbances from the polybutadiene. The presence of the HALS group was indicated by two singlets at 1.2 and 1.3 ppm.

EXAMPLE 17

Preparation of N-(2,2,6,6-tetramethyl-4-piperidinyl)-4-[(4-morpholinyl)carbonyl]phthalimide Into a 125 ml reaction flask equipped with a magnetic stirrer, thermometer, condenser and nitrogen atmosphere were placed 5.0 g (0.013 mol) of acid chloride of Example 2 and 50 ml of 2% dimethylformamide in methylene chloride. Morpholine (4.0 g, 0.046 mol) was added, accompanied by a strong exotherm, and an ice water bath was used to maintain the reaction temperature below 30° C. After complete addition of the morpholine, the reaction was stirred at room temperature for 1 hour then transferred to a separatory funnel with 100 ml methylene chloride and washed with three 50 ml portions of 5% sodium hydroxide and three 50 ml portions of water. The organic solution was dried with anhydrous magnesium sulfate and the solvent stripped using aspirator and high vacuum systems. The product was 4.4 g of white solids. This material was recrystallized from hexanes providing 2.3 g of white crystals melting at 179°–184° C. The infrared spectrum (KBr pellet) showed two carbonyl absorptions at 1710 and 1640 cm$^{-1}$ (imide and amide). The NMR spectrum showed the anticipated aromatic ring (7.5–8.0 ppm, multiplet, 3H), the morpholine ring (3.3–4.0 ppm, broad singlet, 8H) and the HALS group [4.4–4.9 ppm, multiplet, 1H; 0.9–2.3 ppm, several multiplets including two singlets (1.2 and 1.3 ppm)].

EXAMPLE 18

Preparation of N-(2,2,6,6-tetramethyl-4-piperidinyl)-4-{[4-(2,2-di[methoxycarbonyl]ethenyl)phenoxy]carbonyl}phthalimide Into a 125 ml reaction flask equipped with a magnetic stirrer, thermometer, condenser and nitrogen atmosphere were placed 1.9 g (0.005 mol) of acid chloride of Example 2, 50 ml of 2% dimethylformamide in methylene chloride, dimethyl (p-hydroxybenzylidene)malonate (2.6 g, 0.011 mol) and triethylamine (1.0 g, 0.01 mol). The reaction was refluxed for 3 hours then cooled and transferred to a separatory funnel with 100 ml methylene chloride and washed with three 50 ml portions of 5% sodium hydroxide and three 50 ml portions of water. The organic solutions were combined, then dried with anhydrous magnesium sulfate and the solvent stripped using aspirator and high vacuum systems. The product was 5.7 g of slightly yellow solid. This material was heated with a solvent mixture of 20% 2-propanol and 80% hexanes, then cooled and the insoluble material isolated by filtration (2.8 g yellow solid was collected, melting about 135° C.). This was slurried with hot tetrahydrofuran and filtered hot. The tetrahydrofuran was stripped to give 2.4 g of slightly yellow solid melting at 55°–58° C. The infrared spectrum (chloroform) showed a broad carbonyl absorption at 1710 cm$^{-1}$ (imide and ester). The UV spectrum showed an absorbance maximum at 292 nm with molar absorptivity 20000.

EXAMPLE 19

Preparation of N-(2,2,6,6-tetramethyl-4-piperidinyl)-4-{[2-hydroxy-3-(alkyl-[C$_{12-14}$]oxy)propoxy]carbonyl}phthalimide Into a 125 ml reaction flask equipped with a magnetic stirrer, thermometer, condenser and nitrogen atmosphere were placed the HALS-acid of Example 1 (7.0 g (0.021 mol), EPOXIDE 8 ® (a mixture of 1,2-epoxy-3-(alkyl[C$_{12-14}$]oxy)propane, product of Procter and Gamble) (4.3 g), ADOGEN 464 ® (methyltrialkyl[C$_{8-10}$]ammonium chloride, from Ashland Chemical Co.) (0.11 g) and 80 ml of dimethylformamide. The reaction was refluxed for 4 hours and 20 minutes then cooled. The mixture was transferred to a separatory funnel with 200 ml methylene chloride and washed with three 100 ml portions of 5% sodium hydroxide and two 100 ml portions of water. The organic solution was dried with anhydrous magnesium sulfate and the solvent stripped using aspirator and high vacuum systems. The stripped residue still contained residual dimethylformamide and was therefore dissolved in methyl t-butyl ether and washed with three 100 ml portions of water. The organic solution was dried and stripped as before and the residue recrystallized from hexanes, then a second time from 25% aq. ethanol. The recrystallized product was dissolved in methylene chloride and dried and stripped as described previously. The product was next dissolved in 10 ml methylene chloride and precipitated into 600 ml pentane. The product was isolated by filtration as 2.7 g of white crystals melting at 89°-92° C. The infrared spectrum showed a broad carbonyl absorption at 1710 cm$^{-1}$ (imide and ester) and a broad hydroxyl and amine absorption at 3300-3700 cm$^{-1}$.

EXAMPLE 20

Preparation of N-(2,2,6,6-tetramethyl-4-piperidinyl)-4-(n-butoxycarbonyl)phthalimide Into a 125 ml reaction flask equipped with a magnetic stirrer, thermometer, condenser and nitrogen atmosphere were placed the HALS-acid of Example 1 (3.3 g (0.01 mol), n-butylbromide (3.13 g, 0.022 mol), ADOGEN 464 ® (Ashland Chemical Co.) (0.19 g), sodium carbonate (6.64 g, 0.044 mol) and 50 ml of dimethylformamide. The reaction was heated to 80°-90° C. for 2 hours, allowed to stand at ambient temperature for 15 hours then heated again at 80°-90° C. for 6.5 additional hours. The mixture was transferred to a separatory funnel with 100 ml methyl t-butyl ether and 500 ml water. The phases were agitated then allowed to separate. The ether solution was retained and the aqueous solution was extracted with 100 ml fresh ether. The combined ether extracts were dried with anhydrous magnesium sulfate and stripped using aspirator and high vacuum systems. A white solid residue was isolated using a small amount of pentane (the product is quite soluble in this solvent). The product was 3.0 g of white crystals melting at 90°-92° C. The infrared spectrum (chloroform) showed a broad carbonyl absorption at 1700 cm$^{-1}$ (imide and ester). The NMR spectrum showed the anticipated aromatic ring (7.7-8.5 ppm, multiplet, 3H), the —N—C—H and —O—CH$_2$ merged (4.2-4.8, triplet and multiplet, 3H) and the rest of the HALS group and butyl group [0.9-2.3 ppm, several multiplets including two singlets (1.2 and 1.3 ppm)].

EXAMPLE 21

Preparation of N-(2,2,6,6-tetramethyl-4-piperidinyl)-4-(n-octadecyloxycarbonyl)phthalimide Into a suitable flask were placed 7.0 g of octadecanol, 5.7 g triethylamine, 0.1 g of 4-(dimethylamino)pyridine and about 100 ml of dry methylene chloride. The mixture was stirred during the addition of 10.0 g of the acid chloride of Example 2 over a 10 minute period. The reaction was continued at room temperature for 2 hours. The resulting suspension was suction filtered to remove precipitated salt which was washed with fresh methylene chloride. The combined methylene chloride filtrates were placed in a separatory funnel and washed with dilute aq. hydrochloric acid, water and finally with 5% sodium hydroxide. The solution was dried using anhydrous magnesium sulfate and the solvent stripped to yield 14.6 g (97% of theoretical) of a yellow wax. The infrared spectrum of this material showed two carbonyl absorptions (imide and ester) at 1715 and 1725 cm$^{-1}$. The material was examined using liquid chromatography which indicated approximately 4.5% residual octadecanol contaminated the product.

EXAMPLE 22

Reaction of JEFFAMINE ® M-300 with the Acid Chloride of Example 2

Into a suitable flask were placed 4.5 g of JEFFAMINE ® M-300 (an ether and amine terminated polypropylene oxide, a product of Texaco Chemical Company), 3.4 g triethylamine, 0.1 g of 4-(dimethylamino)pyridine and about 100 ml of dry methylene chloride. The mixture was stirred during the addition of 5.0 g of the acid chloride of Example 2 over a 10 minute period. The reaction was allowed to continue at room temperature for 2 hours. The resulting suspension was suction filtered to remove precipitated salt which was washed with fresh methylene chloride. The combined methylene chloride filtrates were placed in a separatory funnel and washed with dilute aqueous hydrochloric acid, water and finally with 5% sodium hydroxide. The solution was dried using anhydrous magnesium sulfate and the solvent stripped to yield 8.3 g (99% of theoretical) of a yellow oil. The infrared spectrum of this material showed two carbonyl absorptions (imide and amide) at 1711 cm$^{-1}$ and 1645 cm$^{-1}$ (broad). The material was examined using liquid chromatography which showed that the high molecular weight material had acquired a UV absorption, an indication that the reaction had proceeded as expected.

EXAMPLE 23

Reaction of the Acid Chloride of Example 2 with DURACARB ® 120

Into a suitable flask were placed 6.1 g of DURACARB ® 120 (a hydroxy-terminated aliphatic polycarbonate product of PPG Industries, having 4.2 wt % hydroxyl groups), 3.4 g triethylamine, 0.1 g of 4-(dimethylamino)pyridine and about 100 ml of dry methylene chloride. The mixture was stirred during the addition of 5.0 g of the acid chloride of Example 2 over a 10 minute period. The reaction was allowed to continue at room temperature for 2 hours. The resulting suspension was suction filtered to remove precipitated salt, which was washed with fresh methylene chloride. The combined methylene chloride filtrates were placed in a separatory funnel and washed with dilute aqueous hydrochloric acid, water and finally, with 5% sodium hydroxide. The solution was dried using anhydrous magnesium sulfate and the solvent stripped to yield 9.5 g (95% of theoretical) of a viscous yellow oil. The infrared spectrum of this material showed two carbonyl absorptions (imide and ester) at 1715 and 1740 cm$^{-1}$. The material was examined using liquid chromatography which showed that the high molecular weight material had acquired an enhanced UV absorption, an indication that the reaction had proceeded as expected.

EXAMPLE 24

Reaction of the Acid Chloride of Example 2 with TONE ® 220

Into a suitable flask were placed 7.5 g of TONE ® 220 (a hydroxy-terminated aliphatic polycaprolactone product of Union Carbide Company, having an assay of 3.4 wt % hydroxyl groups), 3.2 g triethylamine, 0.1 g of 4-(dimethylamino)pyridine and about 100 ml of dry methylene chloride. The mixture was stirred during the addition of 5.0 g of the acid chloride of Example 2 over a 10 minute period. The reaction was allowed to continue at room temperature for 2 hours. The resulting suspension was suction filtered to remove precipitated salt, which was washed with fresh methylene chloride. The combined methylene chloride filtrates were placed in a separatory funnel and washed twice with dilute aqueous hydrochloric acid. During the second wash an emulsion formed that was broken with the addition of sodium chloride. The aqueous acidic washes were back-extracted with fresh methylene chloride. The combined organic solutions were then washed with potassium bicarbonate solution. The solution was dried using anhydrous magnesium sulfate and the solvent stripped to yield 7.1 g (62% of theoretical) of a yellow oil. The infrared spectrum of this material showed a broad carbonyl absorption (imide and ester) at 1700–1750 cm$^{-1}$. The material was examined using liquid chromatography which showed that the high molecular weight material had acquired an enhanced UV absorption, an indication that the reaction had proceeded as expected.

EXAMPLE 25

Reaction of the Acid Chloride of Example 2 with Poly(ethylene glycol), methyl ether Into a suitable flask were placed 5.0 g of poly(ethylene glycol), methyl ether (approximate molecular weight of 350), 3.6 g triethylamine, 5.5 g of the acid chloride of Example 2 and 75 ml of acetone. The reaction was stirred and warmed to a reflux which was continued for a short period. The reaction was allowed to stand at room temperature over night. The resulting suspension was suction filtered to remove precipitated salt and stripped. The residual oil was dissolved in methylene chloride and washed twice with water. The solution was dried using anhydrous magnesium sulfate and the solvent stripped to yield 7.7 g (82% of theoretical) of a viscous yellow oil. The infrared spectrum of this material showed a carbonyl absorption (imide and ester) at 1715 cm$^{-1}$ and a broad C—O absorption at 1100–1110 cm$^{-1}$. The material was examined using liquid chromatography which showed that the high molecular weight material had acquired an enhanced UV absorption, an indication that the reaction had proceeded as expected.

EXAMPLE 26

Preparation of N-(2,2,6,6-tetramethyl-4-piperidinyl)-4-[(2-hydroxy-2-phenylethoxy)carbonyl]phthalimide Into a 125 ml reaction flask equipped with a magnetic stirrer, thermometer, condenser and nitrogen atmosphere were placed the HALS of Example 1 (5.0 g, 0.015 mol), styrene oxide (1.6 g, 0.013 mol), Adogen TM 464 (Ashland Chemical Co.) (0.15 g) and 60 ml of dimethylformamide. The reaction was refluxed for 5 hours then cooled. The mixture was transferred to a separatory funnel with 100 ml methylene chloride and washed with 200 ml of 2.5% sodium hydroxide. Additional methylene chloride, 100 ml, was added and the solution extracted with two 100 ml portions of 5% sodium hydroxide and then 100 ml water. The organic solution was then dried with anhydrous magnesium sulfate and the solvent stripped using aspirator and high vacuum systems. The solid residue (2.9 g) was recrystallized from aqueous ethanol, then recrystallized again from methyl t-butyl ether/hexanes. After high vacuum removal of residual solvent, the product weighed 0.6 g and melted at 144°–146° C. The infrared spectrum (in chloroform) showed a broad carbonyl absorption at 1710 cm$^{-1}$ (imide and ester). The structure of this material was further confirmed using proton NMR spectroscopy.

EXAMPLE 27

Preparation of 4,4,'-[4,13-dihydroxy-1,16-dioxo-2,6,11,15-tetraoxa-hexadecane-1,16-diyl] bis[N-(2,2,6,6-tetramethyl-4-piperidinyl)phthalimide]

Into a 125 ml reaction flask equipped with a magnetic stirrer, thermometer, condenser and nitrogen atmosphere were placed the HALS of Example 1 (4.3 g, 0.013 mol), 1,4-butane diol diglycidyl ether (1.3 g, 0.006 mol), ADOGEN ® 464 (Ashland Chemical Co.) (0.13 g) and 50 ml of dimethylformamide. The reaction was refluxed for 5 hours, then filtered. The filtered mixture was poured into 200 ml water, producing a precipitate. The solution was stirred for 5 minutes then the solid was collected by filtration, slurried with another 500 ml water, stirred 30 minutes, then isolated again. The wet solid was dissolved in tetrahydrofuran and dried with anhydrous magnesium sulfate. The solvent was stripped and the resulting light tan crystals (4.0 g) were recrystallized from about 75 ml of 95% ethanol. The recrystallized solid was dissolved in tetrahydrofuran, dried and stripped as before with additional removal of solvent under high vacuum. The result was 2.4 g of white crystals melting at 117°–122° C. The infrared spectrum (in chloroform) showed a broad carbonyl absorption at 1710 cm$^{-1}$ (imide and ester) and a broad OH and NH absorption at 3100–3600 cm$^{-1}$.

EXAMPLE 28

Preparation of N-(1-acetyl-2,2,6,6-tetramethyl-4-piperidinyl)-4-(ethoxycarbonyl)phthalimide Into a 125 ml reaction flask equipped with a magnetic stirrer, thermometer, condenser and nitrogen atmosphere were placed the HALS of Example 4 (0.9 g, 0.0025 mol), 4-dimethylaminopyridine (0.03 g) and 25 ml of acetic anhydride. The reaction was refluxed for 2 hours, then poured into a beaker containing 200 ml ice water. A brown oil separated immediately and the mixture was stirred until the oil solidified into a tan solid. This solid was isolated by filtration and washed on the filter funnel with several portions of water. The wet solid was dissolved in 50 ml methylene chloride and dried with anhydrous magnesium sulfate. The solvent was stripped to give 0.9 g of light tan crystals melting at 119°–121° C. The infrared spectrum (in chloroform) showed a broad carbonyl absorption at 1710 cm$^{-1}$ (imide and ester) and an amide carbonyl at 1615 cm$^{-1}$.

EXAMPLE 29

Preparation of 4,4'-(4-acetoxy-2,6-dioxa-1,7-dioxoheptane-1,7-diyl)-bis[N-(1-acetyl-2,2,6,6-tetramethyl-4-piperidinyl)phthalimide]

A. Reaction of glycerol acetate bis trimellitate with 2,2,6,6-tetramethyl-4-aminopiperidine Into a 1 liter flask equipped with mechanical stirrer and nitrogen atmosphere were combined glycerol acetate bis trimellitate (33.8 g, 0.07 mol, this ester is available commercially as AC-32, a product of Anhydrides and Chemicals Incorporated) and dimethylformamide (200 ml). This mixture was warmed to 50° C. to dissolve the anhydride and 2,2,6,6-tetramethyl-4-aminopiperdine (25.0 g, 0.16 mol) was added which formed an immediate precipitate. The reaction was stirred for 2 hours while cooling to ambient temperature. Methyl t-butyl ether (400 ml) was added to the mixture and the solid product isolated by filtration. The filtered solid was slurried three times with 300 ml portions of ether and filtered each time. The isolated solid was placed under high vacuum and heated to about 170° C. for 1 hour. The resulting white powder weighed 54.6 g and melted at 203°–207° C. By infrared spectroscopy, this material was identified as the bis amic acid (internal salt) with ester carbonyl banding at 1715 cm$^{-1}$, amide and acid salt carbonyl banding 1540–1620 cm$^{-1}$. Upon heating to 270° C., this amic acid further reacted to form the bis imide. The infrared spectrum had a broad intense carbonyl band at about 1710 cm$^{-1}$ and only small residual banding in the region 1500–1680 cm$^{-1}$.

B. Preparation of the Title Compound

Into a 250 ml flask equipped with reflux condenser were placed the amic acid prepared in step A of this example (10.0 g, 0.013 mol) and 100 ml acetic anhydride. The mixture was refluxed 2 hours, during which time the amic acid slowly went into solution. The reaction mixture was poured into a beaker packed with ice and brought to pH 14 using 45% potassium hydroxide (aqueous). A brown gum separated from solution and was isolated by decanting away the aqueous solution. The gum was dissolved in methylene chloride and transferred to a separatory funnel where it was washed with 10% aqueous sodium hydroxide, 5% aqueous hydrochloric acid and saturated aqueous sodium bicarbonate. The organic phase was dried with anhydrous magnesium sulfate and the solvent was stripped using aspirator and high vacuum systems, yielding 5.6 g of light tan solid. The infrared spectrum of this material showed an intense carbonyl absorption at 1710 cm$^{-1}$ (ester and imide) and another carbonyl absorption at 1620 cm$^{-1}$ (amide).

EXAMPLE 30

Accelerated Weathering of ABS containing N-(2,2,6,6-tetramethyl-4-piperidinyl)-4-(2,2,6,6-tetramethyl-4-piperidinyloxycarbonyl)phthalimide A. Sample Preparation ABS polymer (Dow 500 natural, dried for 4 hours at 90° C.) was used to prepare test specimens for weathering. The ABS compositions prepared were:
1. 0.42 phr HALS of Example 5 and 0.25 phr Tinuvin P
2. 0.25 phr Tinuvin P
3. 0.50 phr Tinuvin P
4. none (control) The additives were first mixed with the polymer and then the blend was extruded twice in a Brabender Prep Center Extruder at 230° C. The control was extruded twice, even though no stabilizer was added. The resulting stabilized polymer was pelletized and molded into plaques on a Newbury 25 ton injection molder at 400° F.

B. Weathering Test

The plaques prepared above were weathered in an Atlas Ci65 Weather-O-Meter using a 6500 watt xenon arc source (inner and outer borosilicate filters, irradiance 0.38 w/m2 at 340 nm) and a cycle time of 3 hours (2 hours of light at 70° C. black panel temperature with 50% relative humidity and a 20 minute front spray during the first hour, and 1 hour dark period at 38° C. with 100% relative humidity and continual back spray). The samples were removed from the test instrument and color development was measured by on a Gardner colorimeter. Increase in yellowness index (YID) was monitored and the values obtained from an average of three samples. The results are shown in TABLE I. These results demonstrate that the use of a hindered amine of this invention in conjunction with a known UV absorber enhances the stability of ABS to accelerated weathering. The effect of the hindered amine (0.42 phr) is distinct from that of the UV absorber (0.25 phr) as demonstrated by controls which show that the UV absorber alone (0.25 phr) and at twice the level (0.50 phr) do not provide the enhanced degree of stabilization observed when the hindered amine is present.

TABLE I

| Accelerated Weathering of ABS Containing HALS | | | | | | | |
|---|---|---|---|---|---|---|---|
| Stabilized Polymer | YID after exposure (days) | | | | | | |
| Composition | 2 | 7 | 14 | 21 | 28 | 35 | 48 |
| 1 | 18.9 | 14.2 | 14.3 | 14.4 | 16.1 | 18.0 | 21.9 |
| 2 | 18.7 | 13.6 | 14.1 | 14.8 | 17.2 | 19.6 | 24.9 |
| 3 | 19.2 | 14.6 | 16.3 | 17.6 | 20.7 | 23.6 | 29.7 |
| 4 | 24.0 | 26.8 | 31.8 | 35.1 | 39.0 | 42.8 | 47.9 |

The present invention may be embodied in other specific forms without departing from the spirit or essential attributes thereof and, accordingly, reference should be made to the appended claims, rather than to the foregoing specification as indicating the scope of the invention.

I claim:

1. A compound of formula

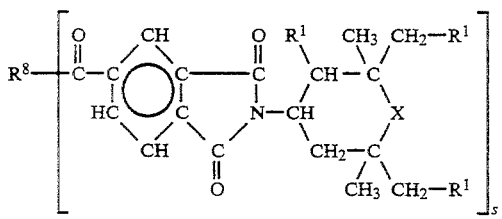

wherein

R¹ is hydrogen or substituted or unsubstituted alkyl of 1-4 carbons;

X is

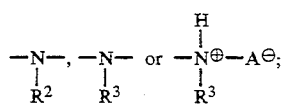

where
- R² is oxyl, hydroxy, substituted or unsubstituted aliphatic acyl of 1-20 carbons, substituted or unsubstituted alicyclic acyl of 6-14 carbons, substituted or unsubstituted aryl acyl of 7-11 carbons, substituted or unsubstituted araliphatic acyl of 7-22 carbons —C(=O)—N(R⁴)(R⁵) or —C(=O)—O—R⁶;
- R³ is hydrogen, substituted or unsubstituted aliphatic of 1-20 carbons, substituted or unsubstituted araliphatic of 7-22 carbons, alkoxyalkyl of 2-21 carbons or —CH₂—C(=O)—O—R⁷;
- R⁴, R⁵ and R⁷ are independently hydrogen, substituted or unsubstituted aliphatic of 1-20 carbons, substituted or unsubstituted aryl of 6-10 carbons, substituted or unsubstituted araliphatic of 7-22 carbons or a substituted or unsubstituted alicyclic group of 5-12 carbons which may optionally contain —N(R⁹)— as a group member and R⁴ and R⁵ may optionally be linked together to form an alicyclic group of 5-7 atoms or may be linked together through a heteroatom —N(R¹⁰)— or —O— to form a heterocyclic ring of 5-7 atoms;
- R⁶ is substituted or unsubstituted aliphatic of 1-20 carbons, substituted or unsubstituted aryl of 6-10 carbons, substituted or unsubstituted araliphatic of 7-22 carbons or a substituted or unsubstituted alicyclic group of 5-12 carbons which may optionally contain —N(R⁹)— as a group member;
- R⁸ is the residue from a substituted or unsubstituted, monofunctional or polyfunctional polymeric alcohol, amine, mercaptan or hydrazine group or molecular mixture thereof, wherein hydroxy-containing, amine-containing, mercaptan-containing and hydrazine-containing polymers may be backbone, pendant or terminally functionalized;
- R⁹ and R¹⁰ are independently hydrogen or substituted or unsubstituted alkyl of 1-4 carbons;
- s is an integer corresponding to the number of free valences of R⁸;
- A is an anion chloride, bromide, sulfate, acid sulfate, sulfite, acid sulfite, p-toluenesulfonate, phenylsulfonate, methylsulfonate, phosphate, acid phosphate, carboxylate from any carboxylic acid or —O⁻;
- substituents for the alkyl, aliphatic, aryl, araliphatic, alicyclic, aliphatic acyl, aryl acyl or araliphatic acyl radicals, R¹, R², R³, R⁴, R⁵, R⁶, R⁷, R⁸, R⁹ and R¹⁰ independently are one or more of aliphatic of 1-8 carbons, alkoxy of 1-4 carbons, alkanoyl of 1-12 carbons, alkanoyloxy of 1-12 carbons, alkoxycarbonyl of 2-5 carbons, arylcarbonyl of 7-11 carbons, acryloyloxy, methacryloyloxy, aryloxy of 6-10 carbons, aralkyl of 7-10 carbons, aryloxycarbonyl of 7-11 carbons, aryl of 6-10 carbons, amino, hydroxy, carboxy, nitrile, chloro, bromo, epoxy, vinyl, alkyl mercapto of 1-4 carbons, benzoyloxy, aryl mercapto of 6-10 carbons, alkylamino of 1-4 carbons, dialkylamino of 2-8 carbons, arylamino of 6-10 carbons, aryl alkyl amino of 7-10 carbons or trialkoxysilyl of 3-9 carbons.

2. The compound of claim 1 wherein
- R¹ is hydrogen or methyl;
- R² is substituted or unsubstituted alkanoyl of 2-5 carbons, aliphatic acyl of 2-5 carbons, substituted or unsubstituted aryl acyl of 7-11 carbons or substituted or unsubstituted araliphatic acyl of 7-22 carbons;
- R³ is hydrogen, substituted or unsubstituted alkyl of 1-4 carbons, substituted or unsubstituted alkoxyalkyl of 2-6 carbons, substituted or unsubstituted araliphatic of 7-10 carbons, allyl or —CH₂—C(=O)—O—R⁷;
- R⁴, R⁵ R⁷ are independently hydrogen, substituted or unsubstituted alkyl of 1-4 carbons, substituted or unsubstituted cyclohexyl, substituted or unsubstituted benzyl or substituted or unsubstituted phenyl; and
- R⁶ is substituted or unsubstituted alkyl of 1-6 carbons, substituted or unsubstituted aralkyl of 7 to 10 carbons or substituted or unsubstituted phenyl.

3. The compound of claim 2 wherein
- R¹ is hydrogen;
- R² is acetyl, substituted or unsubstituted benzoyl or —C(=O)—O—R⁶;
- R³ is hydrogen, substituted or unsubstituted alkyl of 1-4 carbons, allyl, benzyl or —CH₂—C(=O)—O—R⁷.

4. The compound of claim 3 wherein R³ is hydrogen and A is chloride.

5. The compound of claim 3 where R³ is hydrogen and A is —O⁻.

6. The compound of claim 1 wherein R⁸ is one of the following divalent, trivalent or polyvalent polymeric groups (i) or (ii) with the understanding that any valence not satisfied by attachment to the acyl group of general formula I is satisfied by a group R¹⁵:

R¹⁵ is hydrogen, substituted or unsubstituted aliphatic of 1-20 carbons, substituted or unsubstituted aryl of 6-10 carbons, substituted or unsubstituted araliphatic of 7-22 carbons and substituted or unsubstituted alicyclic of 5-12 carbons, substituted or unsubstituted aliphatic acyl of 1-20 carbons, substituted or unsubstituted alicyclic acyl of 6-14 carbons, substituted or unsubstituted aryl acyl of 7-11 carbons or substituted or unsubstituted araliphatic acyl of 7-22 carbons;

(i) —Y—R¹⁶—Y— wherein
Y is —O—, —N(R¹²)—, —S—, —C(=O)—NH—NH—, —NH—NH—, —NH—C(=O)—NH—NH—, —O—C(=O)—NH—NH—, —NH—C(=O)—C(=O)—NH—NH— or —O—C(=O)—C(=O)—NH—NH—;

R¹⁶ is:
poly(alkoxy)dialkyl having a general formula

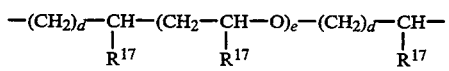

in which $R^{17}$ is hydrogen, substituted or unsubstituted aliphatic of 1–20 carbons or substituted or unsubstituted araliphatic of 7–10 carbons and d is an integer of 1 or 2 and e is an integer of 2–350, polycarbonate diradical having a general formula

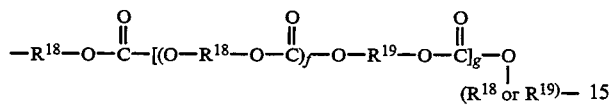

in which f and g are independently integers of 1–5 and $R^{18}$ and $R^{19}$ are independently a substituted or unsubstituted aliphatic diradical of 2–20 carbons, substituted or unsubstituted alicyclic diradical of 5–12 carbons, substituted or unsubstituted aryl diradical of 6–10 carbons or substituted or unsubstituted araliphatic diradical of 7–22 carbons, polyester diradical having a general formula

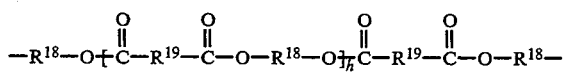

which h is an integer of 1 to 10, polyolefin diradical having a molecular weight of from about 2000 to about 3500;

poly(mercaptoether) diradical having a general formula

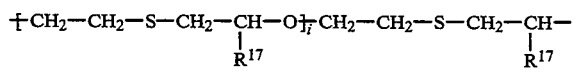

in which i is an integer of 2–12, unsaturated copolymer diradical having a general formula

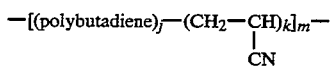

in which m is an integer of 5–10 and j and k are component fractions, k is about 0.1 to about 0.3 and j is 1-k, poly(organosiloxane) diradical having a general formula

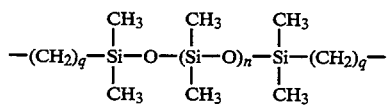

in which n is an integer of 5–3000 and q is an integer of 3 or 4 or polyester diradical having a general formula

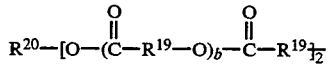

in which b is an integer of 1–10 and may be different for each of the two repeating groups, and $R^{20}$ is an aliphatic diradical of 2 to 4 carbons;

wherein
$R^{21}$ is a
polyester triradical having a general formula

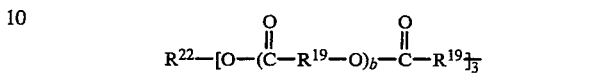

in which b is an integer of 1–10 and may be different for each of the three repeating groups, where $R^{22}$ is an aliphatic triradical of 3 to 8 carbons;

where the substituents for $R^{15}$, $R^{17}$, $R^{18}$ and $R^{19}$ independently are one or more of aliphatic of 1–8 carbons, alkoxy of 1–4 carbons, alkanoyl of 1–12 carbons, alkanoyloxy of 1–12 carbons, alkoxycarbonyl of 2–5 carbons, arylcarbonyl of 7–11 carbons, acryloyloxy, methacryloyloxy, aryloxy of 6–10 carbons, aralkyl of 7–10 carbons, aryloxycarbonyl of 7–11 carbons, aryl of 6–10 carbons, amino, hydroxy, carboxy, nitrile, chloro, bromo, epoxy, vinyl, alkyl mercapto of 1–4 carbons, benzoyloxy, aryl mercapto of 6–10 carbons, alkylamino of 1–4 carbons, dialkylamino of 2–8 carbons, arylamino of 6–10 carbons, aryl alkyl amino of 7–10 carbons or trialkoxysilyl of 3–9 carbons.

7. The compound of claim 1 wherein $R^8$ is a polymeric or copolymeric radical containing recurring units

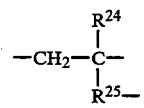

wherein $R^{24}$ is hydrogen, alkyl of 1–4 carbons and phenyl;

$R^{25}$ is —O—, —N($R^{26}$)—, —CH$_2$—O—, —C(=O)—O—CH$_2$—CH(OH)—CH$_2$—O—, —C(=O)—O—CH$_2$—CH$_2$—O— or —C(=O)—O—CH$_2$—CH$_2$—CH$_2$—O—;

$R^{26}$ is hydrogen, substituted or unsubstituted aliphatic of 1–20 carbons, substituted or unsubstituted aryl of 6–10 carbons, substituted or unsubstituted araliphatic of 7–22 carbons or substituted or unsubstituted alicyclic of 5–12 carbons;

the symbol ~ represents the polymer or copolymer backbone in which the units recur with the understanding that any valence not satisfied by attachment to the acyl group of general formula I is satisfied by a group $R^{15}$;

$R^{15}$ is hydrogen, substituted or unsubstituted aliphatic of 1–20 carbons, substituted or unsubstituted aryl of 6–10 carbons, substituted or unsubstituted araliphatic of 7–22 carbons and substituted or unsubstituted alicyclic of 5–12 carbons, substituted or unsubstituted aliphatic acyl of 1–20 carbons, substituted or unsubstituted alicyclic acyl of 6–14 carbons, substituted or unsubstituted aryl acyl of 7–11 carbons or substituted or unsubstituted araliphatic acyl of 7–22 carbons;

wherein the substituents for $R^{15}$ and $R^{26}$ independently are one or more of aliphatic of 1–8 carbons, alkoxy of 1–4 carbons, alkanoyl of 1–12 carbons, alkanoyloxy of 1-12 carbons, alkoxycarbonyl of 2-5 carbons, arylcarbonyl of 7-11 carbons, acryloyloxy, methacryloyloxy, aryloxy of 6-10 carbons, aralkyl of 7-10 carbons, aryloxycarbonyl of 7-11 carbons, aryl of 6-10 carbons, amino, hydroxy, carboxy, nitrile, chloro, bromo, epoxy, vinyl, alkyl mercapto of 1-4 carbons, benzoyloxy, aryl mercapto of 6-10 carbons, alkylamino of 1-4 carbons, dialkylamino of 2-8 carbons, arylamino of 6-10 carbons, aryl alkyl amino of 7-10 carbons or trialkoxysilyl of 3-9 carbons.

8. A compound of formula

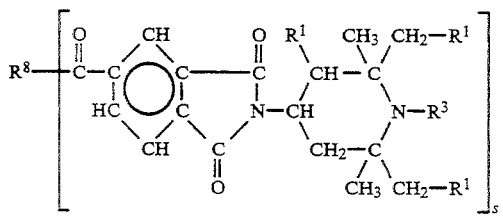

wherein s is an integer corresponding to the number of free valences of $R^8$;

$R^1$ is hydrogen or alkyl of 1-4 carbons;

$R^3$ is hydrogen, substituted or unsubstituted aliphatic of 1-20 carbons, substituted or unsubstituted araliphatic of 7-22 carbons or —CH$_2$—C(=O)—O—$R^7$;

$R^4$, $R^5$ and $R^7$ are independently substituted or unsubstituted aliphatic of 1-20 carbons, substituted or unsubstituted aryl of 6-10 carbons, substituted or unsubstituted araliphatic of 7-22 carbons or a substituted or unsubstituted alicyclic group of 5-12 carbons where the alicyclic group substituents are aliphatic of 1-8 carbons, aralkyl of 7-10 carbons or aryl of 6-10 carbons; or a substituted or unsubstituted heterocyclic group containing 4-6 carbons and one —N($R^9$)— group as a group member and $R^4$ and $R^5$, when neither is alicyclic, may optionally be linked together to form an alicyclic group of 5-7 atoms or may be linked together through a —N($R^{10}$)— group or —O— to form a ring of 5-7 atoms, where the substituents of the heterocyclic groups independently are aliphatic of 1-8 carbons, aralkyl of 7-10 carbons or aryl of 6-10 carbons;

$R^4$ and $R^5$ are additionally, independently hydrogen;

$R^6$ is substituted or unsubstituted aliphatic of 1-20 carbons, substituted or unsubstituted aryl of 6-10 carbons, substituted or unsubstituted araliphatic of 7-22 carbons or a substituted or unsubstituted alicyclic group of 5-12 carbons where the alicyclic group substituents are aliphatic of 1-8 carbons, aralkyl of 7-10 carbons or aryl of 6-10 carbons; or a substituted or unsubstituted heterocyclic group containing 4-6 carbons and one —N($R^9$)— group as a group member where the substituents of the heterocyclic groups independently are aliphatic of 1-8 carbons, aralkyl of 7-10 carbons or aryl of 6-10 carbons;

$R^8$ is one of the following divalent, trivalent and polyvalent polymeric groups (i)-(iii) with the understanding that any valence not satisfied by attachment to the acyl group of general formula I is satisfied by a group $R^{15}$:

$R^{15}$ is hydrogen, substituted or unsubstituted aliphatic of 1-20 carbons, substituted or unsubstituted aryl of 6-10 carbons, substituted or unsubstituted araliphatic of 7-22 carbons and substituted or unsubstituted alicyclic of 5-12 carbons, substituted or unsubstituted aliphatic acyl of 1-20 carbons, substituted or unsubstituted alicyclic acyl of 6-14 carbons, substituted or unsubstituted aryl acyl of 7-11 carbons or substituted or unsubstituted araliphatic acyl of 7-22 carbons;

(i) —Y—$R^{16}$—Y— wherein

Y is —O—, —N($R^{12}$)—, —S—, —C(=O) —NH—NH—, —NH—NH—, —NH—C(=O)—NH—NH—, —O—C(=O)—NH—NH—, —NH—C(=O)—C(=O)—NH—NH— or —O—C(=O)—C(=O)—NH—NH—;

$R^{16}$ is a poly(alkoxy)dialkyl diradical, a polycarbonate diradical, a diester diradical, a polyester diradical, a poly(mercaptoether) diradical, an unsaturated polyolefin diradical having a molecular weight of from about 2000 to about 3500;

an unsaturated copolymer diradical having a formula

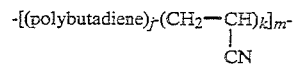

in which m is an integer of 5-10 and j and k are component fractions, k is about 0.1 to about 0.3 and j is 1-k; or a poly(organosiloxane) diradical;

(ii)

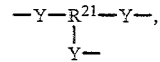

wherein $R^{21}$ is a polyester triradical;

(iii) a polymeric or copolymeric radical containing recurring units

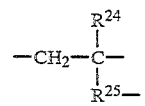

wherein $R^{24}$ is hydrogen, alkyl of 1-4 carbons and phenyl;

$R^{25}$ is —O—, —N($R^{26}$)—, —CH$_2$—O—, —C(=O)—O—CH$_2$—CH(OH)—CH$_2$—)—, —C(=O)—O—CH$_2$—CH$_2$—O— or —C(=O)—O—CH$_2$—CH$_2$—CH$_2$—O—;

$R^{26}$ is hydrogen, substituted or unsubstituted aliphatic of 1-20 carbons, substituted or unsubstituted aryl of 6-10 carbons, substituted or unsubstituted araliphatic of 7-22 carbons or substituted or unsubstituted alicyclic of 5-12 carbons;

the symbol ~ represents the polymer or copolymer backbone in which the units recur;

$R^9$ and $R^{10}$ are independently hydrogen or substituted or unsubstituted alkyl of 1-4 carbons where the alkyl substituents are aryl of 6-10 carbons or vinyl;

$R^{12}$ is hydrogen, substituted or unsubstituted aliphatic of 1-20 carbons, substituted or unsubstituted aryl of 6-10 carbons, substituted or unsubstituted araliphatic of 7-22 carbons or a substituted or unsubstituted alicyclic group of 5-12 carbons where the alicyclic group substituents are aliphatic of 1–8 carbons, aralkyl of 7–10 carbons or aryl of 6–10 carbons; or a substituted or unsubstituted heterocyclic group containing 4–6 carbons and one —N(R$^{1-4}$)— group as a group member where the heterocyclic group substituents are aliphatic of 1–8 carbons, aralkyl of 7–10 carbons or aryl of 6–10 carbons;

R$^{14}$ is hydroxy, substituted or unsubstituted aliphatic acyl of 1–20 carbons, substituted or unsubstituted alicyclic acyl of 6–14 carbons where the alicyclic acyl group substituents are aliphatic of 1–8 carbons, aralkyl of 7–10 carbons or aryl of 6–10 carbons, substituted or unsubstituted aryl acyl of 7–11 carbons, substituted or unsubstituted araliphatic acyl of 7–22 carbons, —C(=O)—N(R$^4$)(R$^5$), —C(=O)—O—R$^6$, substituted or unsubstituted aliphatic of 1–20 carbons, substituted or unsubstituted araliphatic radical of 7–22 carbons, or —CH$_2$—C(=O)—O—R$^7$;

where additional independent substituents for the aliphatic, aryl, araliphatic and alicyclic groups in R$^3$, R$^4$, R$^5$, R$^6$, R$^7$, R$^{12}$ and R$^{15}$; and for the alkyl groups of R$^9$ and R$^{10}$; and for the heterocyclic groups containing 4–6 carbons and either one —N(R$^9$)— group or one —N(R$^{14}$)— group in R$^4$, R$^5$, R$^6$, R$^7$ and R$^{12}$;

may be one or more of alkoxy of 1–4 carbons, alkanoyl of 1–12 carbons, alkanoyloxy of 1–12 carbons, alkoxycarbonyl of 2–5 carbons, arylcarbonyl of 7–11 carbons, acryloyloxy, methacryloyloxy, aryloxy of 6–10 carbons, aryloxycarbonyl of 7–11 carbons, amino, hydroxy, carboxy, nitrile, chloro, bromo, epoxy, alkyl mercapto of 1–4 carbons, benzoyloxy, aryl mercapto of 6–10 carbons, alkylamino of 1–4 carbons, dialkylamino of 2–8 carbons, arylamino of 6–10 carbons, aryl alkyl amino of 7–10 carbons or trialkoxysilyl of 3–9 carbons.

9. The compound of claim 8 wherein the poly(alkoxy)dialkyl diradical has a formula

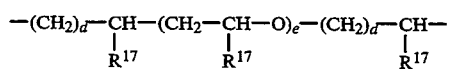

in which R$^{17}$ is hydrogen, substituted or unsubstituted aliphatic of 1–20 carbons or substituted or unsubstituted araliphatic of 7–10 carbons and e is an integer of 2–350;

the polycarbonate diradical has a formula

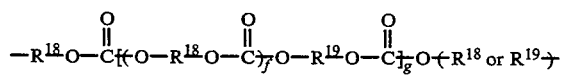

in which f and g are independently integers of 1–5 and R$^{18}$ and R$^{19}$ are independently a substituted or unsubstituted aliphatic diradical of 2–20 carbons, substituted or unsubstituted alicyclic diradical of 5–12 carbons, substituted or unsubstituted aryl diradical of 6–10 carbons or substituted or unsubstituted araliphatic diradical of 7–22 carbons;

the diester or polyester diradical has a formula

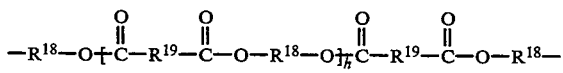

in which h is an integer of 1 to 10, or a formula

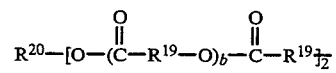

in which b is an integer of 1–10 and may be different for each of the two repeating groups, and R$^{20}$ is an aliphatic diradical of 2 to 4 carbons;

the poly(mercaptoether) diradical has a formula

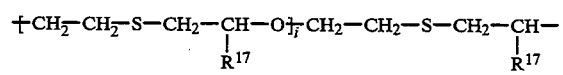

in which i is an integer of 2–12;

the poly(organosiloxane) diradical has a formula

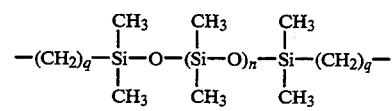

in which n is an integer of 5–3000 and q is an integer of 3 or 4; and the polyester triradical has a formula

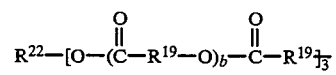

in which b is an integer of 1–10 and may be different for each of the three repeating groups, where R$^{22}$ is an aliphatic triradical of 3 to 8 carbons;

where additional independent substituents for the aliphatic, aryl, araliphatic and alicyclic groups in R$^{18}$, R$^{19}$ and R$^{20}$; and for the aliphatic and araliphatic groups in R$^{17}$; and for the aliphatic groups in R$^{20}$ and R$^{22}$; may be one or more of alkoxy of 1–4 carbons, alkanoyl of 1–12 carbons, alkanoyloxy of 1–12 carbons, alkoxycarbonyl of 2–5 carbons, arylcarbonyl of 7–11 carbons, acryloyloxy, methacryloyloxy, aryloxy of 6–10 carbons, aryloxycarbonyl of 7–11 carbons, amino, hydroxy, carboxy, nitrile, chloro, bromo, epoxy, alkyl mercapto of 1–4 carbons, benzoyloxy, aryl mercapto of 6–10 carbons, alkylamino of 1–4 carbons, dialkylamino of 2–8 carbons, arylamino of 6–10 carbons, aryl alkyl amino of 7–10 carbons or trialkoxysilyl of 3–9 carbons.

10. The compound of claim 8 wherein

R$^1$ is hydrogen or methyl;

R$^3$ is hydrogen, substituted or unsubstituted alkyl of 1–4 carbons, substituted or unsubstituted alkoxyalkyl of 2–6 carbons, substituted or unsubstituted araliphatic of 7–10 carbons, allyl or —CH$_2$—C(=O)—O—R$^7$;

R$^4$, R$^5$ and R$^7$ are independently substituted or unsubstituted alkyl of 1–4 carbons, substituted or unsubstituted cyclohexyl, substituted or unsubstituted benzyl or substituted or unsubstituted phenyl;

R$^4$ R$^5$ and are independently hydrogen; and

R$^6$ is substituted or unsubstituted alkyl of 1–6 carbons, substituted or unsubstituted aralykl of 7–10 carbons or substituted or unsubstituted phenyl.

11. The compound of claim 10 wherein

R$^1$ is hydrogen;

R³ is hydrogen, substituted or unsubstituted alkyl of 1–4 carbons, allyl, benzyl or —CH₂—C(=O)—O—R⁷.

12. The compound of claim 11 wherein R³ is hydrogen.

13. The compound of claim 8 which is styrene/allyl alcohol/N-(2,2,6,6-tetramethyl-4-piperidinyl)-4-allyloxy-carbonylphthalimide copolymer; N-(2,2,6,6-tetramethyl-4-piperidinyl)-4-[octylphenoxypoly(ethoxy)carbonyl]phthalimide; N-(2,2,6,6-tetramethyl-4-piperidinyl)phthalimide-4-carbonyl endcapped poly(butadiene) diol; N-(2,2,6,6-tetramethyl-4-piperidinyl)phthalimide-4-carboxamido endcapped polypropylene oxide; N-(2,2,6,6-tetramethyl-4-piperidinyl)phthalimide-4-carbonyl endcapped hydroxy-terminated aliphatic polycarbonate; N-(2,2,6,6-tetramethyl-4-piperidinyl)phthalimide-4-carbonyl endcapped aliphatic polycaprolactone diol; or N-(2,2,6,6-tetramethyl-4-piperidinyl)phthalimide-4-carbonyl endcapped poly(ethylene glycol) monomethyl ether.

14. A process of stabilizing a synthetic or natural polymer composition against the degradative effects of heat or light by mixing with the polymer composition a compound of claim 1 in an amount effective to stabilize the polymer composition against the degradative effects of heat or light.

15. A polymeric composition stabilized against the degradative effects of heat or light comprising a synthetic or natural polymer mixed with a compound of claim 1 in an amount effective to stabilize the polymer against the degradative effects of heat or light.

* * * * *